(12) United States Patent
Dorman

(10) Patent No.: US 12,063,433 B2
(45) Date of Patent: Aug. 13, 2024

(54) ORIENTATION CALIBRATION SYSTEM FOR IMAGE CAPTURE

(71) Applicant: Circinus Medical Technology LLC, Concord, MA (US)

(72) Inventor: John Kyle Dorman, Midland, TX (US)

(73) Assignee: Circinus Medical Technology LLC, Concord, MA (US)

( * ) Notice: Subject to any disclaimer, the term of this patent is extended or adjusted under 35 U.S.C. 154(b) by 258 days.

(21) Appl. No.: 17/604,362

(22) PCT Filed: Apr. 15, 2020

(86) PCT No.: PCT/US2020/028375
§ 371 (c)(1),
(2) Date: Oct. 15, 2021

(87) PCT Pub. No.: WO2020/214744
PCT Pub. Date: Oct. 22, 2020

(65) Prior Publication Data
US 2022/0201199 A1    Jun. 23, 2022

Related U.S. Application Data

(60) Provisional application No. 62/834,384, filed on Apr. 15, 2019.

(51) Int. Cl.
*H04N 17/02* (2006.01)
*A61B 90/00* (2016.01)
(Continued)

(52) U.S. Cl.
CPC .......... *H04N 23/64* (2023.01); *A61B 90/361* (2016.02); *A61B 90/37* (2016.02); *H04N 17/002* (2013.01); *H04N 23/633* (2023.01)

(58) Field of Classification Search
CPC .... H04N 23/64; H04N 23/633; H04N 17/002; A61B 90/361; A61B 90/37
(Continued)

(56) References Cited

U.S. PATENT DOCUMENTS

| | | |
|---|---|---|
| 5,143,076 A | 9/1992 | Hardy et al. |
| 5,603,318 A | 2/1997 | Heilbrun et al. |

(Continued)

FOREIGN PATENT DOCUMENTS

| | | |
|---|---|---|
| CN | 101198958 A | 6/2008 |
| CN | 101528122 A | 9/2009 |

(Continued)

OTHER PUBLICATIONS

International Patent Appl. No. PCT/US2022/022204, International Search Report and Written Opinion dated Jun. 10, 2022, 18 pgs.

(Continued)

*Primary Examiner* — Trang U Tran
(74) *Attorney, Agent, or Firm* — Foley & Lardner LLP

(57) ABSTRACT

Orientation calibration system for image capture is disclosed that may include a camera to capture a target image, a display screen to display the image, an orientation sensor to determine at least two axes of orientation of the system, and a processor. The processor configured to determine the present orientation of the system using the orientation sensor, display a portion of present and a desired orientation of the system, receive a request to capture the target image, and capture the target image using the camera in response to receiving the request to capture the target image, and when a difference between the present orientation of the system and desired orientation of system is within a threshold. The system may be used to adjust/orient a display monitor to ensure desired alignment to accurately capture image. Meth- (Continued)

ods for aligning/orienting a display monitor (imaging source), and the orientation calibration system are provided.

10 Claims, 30 Drawing Sheets

(51) Int. Cl.
*H04N 17/00* (2006.01)
*H04N 23/60* (2023.01)
*H04N 23/63* (2023.01)

(58) Field of Classification Search
USPC .......................................................... 348/77
See application file for complete search history.

(56) References Cited

U.S. PATENT DOCUMENTS

| | | | |
|---|---|---|---|
| 5,824,085 A | 10/1998 | Sahay et al. | |
| 5,880,976 A | 3/1999 | Digioia, III et al. | |
| 6,129,670 A | 10/2000 | Burdette et al. | |
| 6,139,544 A | 10/2000 | Mikus et al. | |
| 6,246,474 B1 | 6/2001 | Cerni et al. | |
| 6,511,236 B1 | 1/2003 | Webjorn et al. | |
| 6,638,281 B2 | 10/2003 | Gorek | |
| RE40,176 E | 3/2008 | Peshkin et al. | |
| 7,611,522 B2 | 11/2009 | Gorek | |
| 8,086,077 B2 | 12/2011 | Eichhorn | |
| 8,442,621 B2* | 5/2013 | Gorek .................... | A61B 90/39 606/97 |
| 9,119,572 B2 | 9/2015 | Gorek et al. | |
| 9,585,700 B2 | 3/2017 | Wehrle et al. | |
| 10,064,687 B2 | 9/2018 | Haimerl et al. | |
| 10,123,840 B2 | 11/2018 | Dorman | |
| 10,342,619 B2 | 7/2019 | Bracke et al. | |
| 10,561,466 B2 | 2/2020 | Hedblom et al. | |
| 10,602,114 B2 | 3/2020 | Casas | |
| 10,864,023 B2 | 12/2020 | Pak et al. | |
| 11,000,335 B2 | 5/2021 | Dorman | |
| 11,191,592 B2 | 12/2021 | Gorek et al. | |
| 11,484,381 B2 | 11/2022 | Pak et al. | |
| 11,826,111 B2 | 11/2023 | Mahfouz | |
| 11,832,886 B2 | 12/2023 | Dorman | |
| 2002/0035323 A1 | 3/2002 | Saha et al. | |
| 2002/0077540 A1 | 6/2002 | Kienzle, III | |
| 2002/0120252 A1 | 8/2002 | Brock et al. | |
| 2002/0140694 A1 | 10/2002 | Sauer et al. | |
| 2003/0181919 A1 | 9/2003 | Gorek | |
| 2003/0199882 A1 | 10/2003 | Gorek | |
| 2003/0236548 A1 | 12/2003 | Hovanes et al. | |
| 2004/0068187 A1 | 4/2004 | Krause et al. | |
| 2005/0113846 A1 | 5/2005 | Carson | |
| 2006/0004322 A1 | 1/2006 | Uesugi et al. | |
| 2007/0276397 A1 | 11/2007 | Tacheco | |
| 2008/0057889 A1 | 3/2008 | Jan | |
| 2008/0086160 A1 | 4/2008 | Mastri et al. | |
| 2008/0200927 A1 | 8/2008 | Hartmann et al. | |
| 2009/0157083 A1 | 6/2009 | Park et al. | |
| 2009/0163901 A1 | 6/2009 | Fisher et al. | |
| 2009/0270868 A1 | 10/2009 | Park et al. | |
| 2009/0292201 A1 | 11/2009 | Kruecker | |
| 2009/0292279 A1 | 11/2009 | Bliweis et al. | |
| 2009/0311655 A1 | 12/2009 | Karkanias et al. | |
| 2010/0100081 A1 | 4/2010 | Tuma et al. | |
| 2010/0153081 A1 | 6/2010 | Bellettre et al. | |
| 2010/0198402 A1 | 8/2010 | Greer et al. | |
| 2010/0210939 A1 | 8/2010 | Hartmann et al. | |
| 2010/0274256 A1* | 10/2010 | Ritchey .................... | A61L 2/081 606/96 |
| 2011/0098721 A1 | 4/2011 | Tran et al. | |
| 2011/0214279 A1 | 9/2011 | Park et al. | |
| 2011/0268248 A1 | 11/2011 | Simon et al. | |
| 2012/0116203 A1 | 5/2012 | Vancraen et al. | |
| 2012/0150243 A9 | 6/2012 | Crawford et al. | |
| 2012/0232834 A1 | 9/2012 | Roche et al. | |
| 2012/0319859 A1 | 12/2012 | Taub et al. | |
| 2013/0085344 A1 | 4/2013 | Merkl et al. | |
| 2013/0095855 A1 | 4/2013 | Bort | |
| 2013/0114866 A1 | 5/2013 | Kasodekar et al. | |
| 2013/0245461 A1 | 9/2013 | Maier-Hein et al. | |
| 2013/0253599 A1 | 9/2013 | Gorek et al. | |
| 2014/0148808 A1 | 5/2014 | Inkpen et al. | |
| 2015/0010220 A1 | 1/2015 | Teichman et al. | |
| 2016/0022374 A1 | 1/2016 | Haider et al. | |
| 2016/0106202 A1 | 4/2016 | Ford | |
| 2016/0235481 A1 | 8/2016 | Dorman | |
| 2016/0250040 A1 | 9/2016 | Hermle et al. | |
| 2016/0324580 A1 | 11/2016 | Esterberg | |
| 2016/0373647 A1 | 12/2016 | Garcia Morate et al. | |
| 2017/0007328 A1 | 1/2017 | Cattin et al. | |
| 2017/0027651 A1 | 2/2017 | Esterberg | |
| 2017/0035517 A1 | 2/2017 | Geri et al. | |
| 2017/0071673 A1 | 3/2017 | Ferro et al. | |
| 2017/0135706 A1 | 5/2017 | Frey et al. | |
| 2017/0172696 A1 | 6/2017 | Saget et al. | |
| 2017/0202633 A1 | 7/2017 | Liu | |
| 2017/0221244 A1 | 8/2017 | Hiraga et al. | |
| 2017/0245947 A1 | 8/2017 | Bozung et al. | |
| 2017/0333134 A1 | 11/2017 | Wollowick et al. | |
| 2018/0000380 A1* | 1/2018 | Stein ...................... | A61B 90/37 |
| 2018/0008358 A1 | 1/2018 | Kostrzewski et al. | |
| 2018/0140362 A1 | 5/2018 | Cal et al. | |
| 2018/0303559 A1 | 10/2018 | Shepherd et al. | |
| 2018/0310956 A1 | 11/2018 | Polster | |
| 2019/0029757 A1 | 1/2019 | Roh et al. | |
| 2019/0046278 A1 | 2/2019 | Steinle et al. | |
| 2019/0060000 A1 | 2/2019 | Dorman | |
| 2019/0090959 A1 | 3/2019 | Haider et al. | |
| 2019/0336179 A1 | 11/2019 | Pak et al. | |
| 2019/0357809 A1 | 11/2019 | Borja | |
| 2019/0388173 A1 | 12/2019 | Pak et al. | |
| 2020/0051274 A1 | 2/2020 | Siemionow et al. | |
| 2020/0111213 A1 | 4/2020 | Chacon et al. | |
| 2020/0197191 A1 | 6/2020 | Akhlaghpour et al. | |
| 2020/0229869 A1 | 7/2020 | Dorman | |
| 2020/0305985 A1 | 10/2020 | Tolkowsky | |
| 2021/0100536 A1 | 4/2021 | Spindle | |
| 2021/0186617 A1 | 6/2021 | Gorek et al. | |
| 2021/0228279 A1 | 7/2021 | Dorman | |
| 2022/0192756 A1 | 6/2022 | Dorman | |
| 2022/0237817 A1 | 7/2022 | Dorman | |
| 2022/0241018 A1 | 8/2022 | Dorman | |
| 2022/0351410 A1 | 11/2022 | Siemionow et al. | |
| 2023/0036038 A1 | 2/2023 | Finley et al. | |
| 2023/0131831 A1 | 4/2023 | Dorman | |
| 2023/0172631 A1 | 6/2023 | Richter et al. | |
| 2023/0346481 A1 | 11/2023 | Dorman | |

FOREIGN PATENT DOCUMENTS

| | | |
|---|---|---|
| CN | 101721231 A | 6/2010 |
| CN | 101984931 A | 3/2011 |
| CN | 103519895 A | 1/2014 |
| EP | 2 901 957 A1 | 8/2015 |
| KR | 101478522 B1 | 1/2015 |
| KR | 101901521 B1 | 9/2018 |
| WO | WO-2013/020026 | 2/2013 |
| WO | WO-2014/025305 A1 | 2/2014 |
| WO | WO-2014/063181 A1 | 5/2014 |
| WO | WO-2015/168781 | 11/2015 |
| WO | WO-2016/007936 | 1/2016 |
| WO | WO-2016/131016 A2 | 8/2016 |
| WO | WO-2017/167799 A1 | 10/2017 |
| WO | WO-2019/036524 A1 | 2/2019 |
| WO | WO-2020/214645 A1 | 10/2020 |
| WO | WO-2020/214744 A1 | 10/2020 |
| WO | WO-2022/109185 A1 | 5/2022 |

OTHER PUBLICATIONS

International Search Report and Written Opinion for International Patent Application PCT/US2022/024683 dated Jun. 21, 2022.

(56) References Cited

OTHER PUBLICATIONS

U.S. Appl. No. 17/233,301, filed Apr. 16, 2021, System and Method for Medical Device Placement in Bone.
U.S. Appl. No. 17/604,359, filed Oct. 15, 2021, Attachment Apparatus to Secure a Medical Alignnient Device to Align a Tool.
International Pat. Appl. No. PCT PCT/US2021/059965, International Search Report and Written Opinion dated Feb. 3, 2022, 7 pgs.
International Pat. Appl. No. PCT/US2020/028220, International Search Report and Written Opinion, dated Aug. 14, 2020, 22 pgs.
International Search Report and Written Opinion in corresponding international application No. PCT/US2016/017897, mailed Aug. 24, 2016, 13 pages.
International Search Report and Written Opinion in PCT/US18/46786, dated Dec. 13, 2018, 10 pgs.
International Search Report and Written Opinion issued in PCT/US2022/014988 Dtd Apr. 6, 2022, 17 pages.
Merloz et al., "Pedicle Screw Placement Using Image Guided Techniques." Clinical Orthopaedics and Related Research, No. 354, pp. 39-48, 1998, entire document [online] URL=https://journals.lww.com/clinorthop/Fulltext/1998/09000/Pedicle_Screw_Placement_Using_Image_Guided.6.aspx.
Supplementary Partial European Search Report corresponding to EP 18846995.1 dated Jun. 11, 2021, 4 pages.
International Search Report and Written Opinion corresponding to PCT/US2020/028375, dated Jul. 21, 2020, 10 pages.
Harrison, Peter, Simpler Line Follower Sensors, Micromouse Online, Apr. 15, 2011, https://web.archive.org/web/20120422001123 /https://micromouseonline.com/2011/04/15/simpler-line-follower-sensors/. (Year: 2011), 3 pgs.
NumPy—Data Types, tutorialspoint, https://web.archive.org/web/20181126133733/https://www.tutorialspoint.com/numpy/numpy_data_type.htm. 2018 (Year: 2018), 8 pgs.
U.S. Appl. No. 18/513,155, filed Nov. 17, 2023, Circinus Medical Technology LLC.
U.S. Appl. No. 18/553,025, filed Sep. 28, 2023, Circinus Medical Technology LLC.
U.S. Appl. No. 18/554,969, filed Oct. 11, 2023, Circinus Medical Technology LLC.
Julian Horsey, "Ozaki iCoat Finger Case Makes Draw Something Even More Fun", Apr. 20, 2012, pp. 1-11, XP093028330, Retrieved from the Internet: URL:https://www.geeky-gadgets.com/ozaki-icoat-finger-case-makes-draw-someting-even-more-fun-Apr. 20, 2012/ [retrieved on Mar. 2, 2023].
International Search Report and Written Opinion on PCT/US2022/047306 Dated Mar. 28, 2023.
U.S. Appl. No. 16/639,107, filed Feb. 13, 2020, System and Method Using Augmented Reality With Shape Alignment for Medical Device Placement in Bone.
U.S. Appl. No. 17/233,301, filed Apr. 16, 2021, System and Method for Medical Device Placement.
U.S. Appl. No. 17/604,359, filed Oct. 15, 2021, Attachment Apparatus to Secure a Medical Alignment Device to Align a Tool.
U.S. Appl. No. 17/530,311, filed Nov. 18, 2021, Systems and Methods for Artificial Intelligence Based Image Analysis for Placement of Surgical Appliance.
U.S. Appl. No. 17/591,478, filed Feb. 2, 2022, Systems and Methods for Simulating Three-Dimensional Orientations of Surgical Hardware Devices About an Insertion Point of an Anatomy.
U.S. Appl. No. 17/970,378, filed Oct. 20, 2022, Attachment Apparatus to Secure a Medical Alignment Device to Align a Tool.
U.S. Appl. No. 18/350,672, filed Jul. 11, 2023, System and Method for Medical Device Placement.
U.S. Appl. No. 16/639,107, filed Feb. 13, 2020, System and Method Using Augmented Reality With Shape Alignment for Medical Device Placement.
U.S. Appl. No. 18/553,025, filed Sep. 28, 2023, System and Method for Simulating an Orientation of a Medical Device at an Insertion Point.
U.S. Appl. No. 18/554,969, filed Oct. 11, 2023, System and Method for Lidar-Based Anatomical Mapping.
Crescendo CR-30 phone holder. Amazon datasheet [online]. Crescendo, first available on Nov. 18, 2017. [Retrieved on Jun. 13, 2024]; Retrieved from the Internet. <URL: https://a.co/d/fyEOcbM>.

* cited by examiner

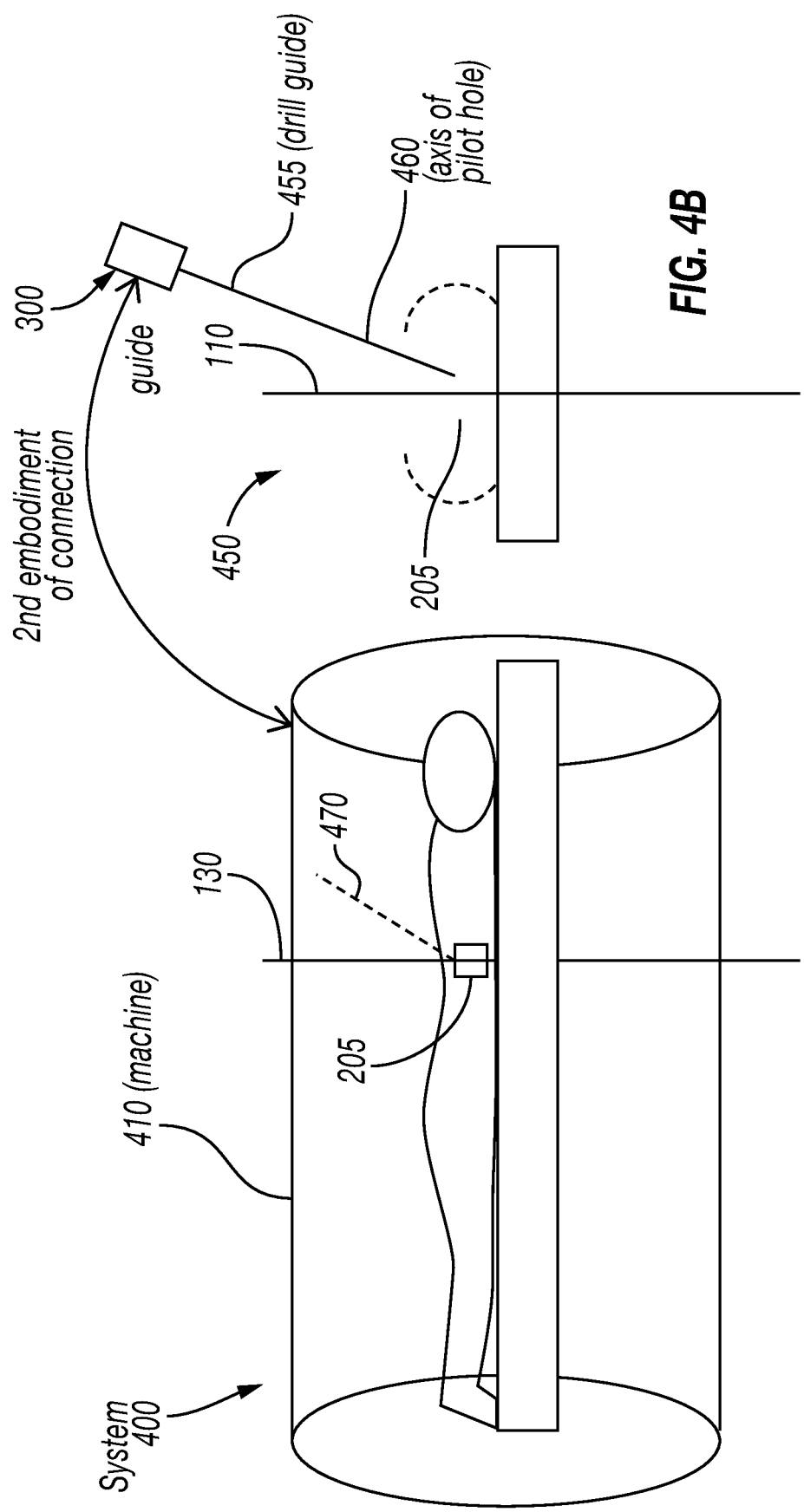

ions of the orientation calibration system and the external monitor change relative to one another, and to display a front/back graphical indicator when the first side of the orientation calibration system is positioned along a side edge of the external monitor to display an indication from the orientation sensor of the present front/back orientation of the orientation calibration system and a desired front/back orientation of the external monitor, wherein the front/back graphical indicator changes as the front/back orientations of the orientation calibration system and the external monitor change relative to one another.

ORIENTATION CALIBRATION SYSTEM FOR IMAGE CAPTURE

CROSS-REFERENCE TO RELATED PATENT APPLICATIONS

This application is a U.S. National Phase Application under 35 U.S.C. § 371 of International Application No. PCT/US2020/028375, filed Apr. 15, 2020, which claims the benefit of priority to U.S. Provisional Application No. 62/834,384, filed on Apr. 15, 2019, both of which are incorporated herein by reference in their entirety.

TECHNICAL FIELD

This application claims the benefit of and priority to U.S. Provisional Patent Application Ser. No. 62/834,384 filed on Apr. 15, 2019, entitled "SYSTEM TO CALIBRATE ORIENTATION OF A MEDICAL ALIGNMENT DEVICE AND AN IMAGING SOURCE" and naming John Kyle Dorman as the inventor, the entirety of which is incorporated herein by reference for all purposes.

This disclosure relates generally to an orientation calibration system for image capture for use in any application, but such system is illustrated herein in the context of use with a medical alignment device. For example, the orientation calibration system of this disclosure, and related methods, may be used to properly and accurately capture diagnostic images for use with a medical alignment device that generates alignment angles (such as a three-dimensional alignment angle) as output that facilitates the alignment and orientation of surgical equipment, tools, and/or hardware during surgery when inserting a medical device in a bone. In one implementation, such surgical equipment or tools may be used to create a pilot hole or tract in a vertebra for receiving a pedicle screw at a precise orientation, such as a three-dimensional alignment angle.

BACKGROUND

When images are captured using an image capture device, such as a camera, the angle in which the image is captured may skew or alter critical details of the image. This could, for example, cause unintended consequences if such altered critical details are used in connection with images used for medical procedures or for diagnoses. For example, in connection with spinal fusion surgery, these patients may have pedicle screws placed into their vertebrae. The pedicle screws are typically implanted into the vertebrae through the pedicles of the vertebrae. A pilot hole may be created through the cortex of the bone to create the path or tract through which the pedicle screw will be placed. Placing the pedicle screw at the correct angle helps to ensure a mechanically sound construct and to avoid injury to surrounding structures such as the spinal cord, nerve roots, and blood vessels. The orientation of the pedicle screw can be described by a three-dimensional alignment angle or insertion angle, and the correct image capture of any diagnostic images used in determining such an alignment insertion angle needs to be properly and accurately performed.

Other situations in which having a true alignment and image capture of an object or the subject is important. Examples include construction, interior design, CAD drawings, and three-dimensional printing. Another example, as mentioned above, is a surgical navigation system in which having a true and accurate angle is a prerequisite for safe functioning. If the camera or image capture is held at an angle, in any plane, the resulting photo will not be truly orthogonal. Sometimes the problem may be corrected with image processing software in the post-processing phase provided the image has a straight line, or edge, but this cannot be guaranteed. Often times the subject of the image does not have a straight line or edge, like an axial CT for example. In this case, it is imperative that the camera, which can be an iPhone or iPod touch, be held orthogonal in all planes at the time the image is captured so as not to introduce skew and error.

SUMMARY

This summary is provided to introduce a selection of elements and aspects that are further described below in the detailed description. This summary is not intended to identify key or essential features of the claimed subject matter, nor is it intended to be used as an aid in limiting the scope of the claimed subject matter.

In a first general aspect, an orientation calibration system for image capture is provided that ensures that the camera of the device, which may be implemented on a smartphone, iPhone, iPod touch, or other electronic device, tablet, or tablet like device, captures an image while being orthogonal in all planes.

In one general aspect, an orientation calibration system for image capture is provided, and this may be implemented or referred to as a medical alignment device. The orientation calibration system may be configured to be oriented to capture a target image, which may be referred to as a reference image. The orientation calibration system may include a camera operable to capture a target image, a display screen configured to display the target image captured using the camera, and an orientation sensor configured to determine two (or three axes of rotation in certain other embodiments) of the orientation calibration system. The orientation calibration system may include one or more processors to determine a present orientation of the orientation calibration system using the orientation sensor, to display at least a portion of the present orientation of the orientation calibration system and a desired orientation of the orientation calibration system on the display screen, to receive a request to capture the target image, and to capture the target image using the camera in response to receiving the request to capture the target image, and when a difference between the present orientation of the orientation calibration system and the desired orientation of the orientation calibration system is within a threshold.

In another general aspect, an orientation calibration system for image capture is provided for use in aligning an image source that displays the target image. For example, the target image that is being captured is displayed on an external monitor having four sides with each adjacent side being orthogonal to one another, and the orientation calibration system includes a first side and a back side, and is configured to assist in aligning/orienting the external monitor in an orthogonal or desired orientation or position relative to the ground before the target image is captured by the orientation calibration system. The one or more processors of the orientation calibration system may be configured to display a left/right graphical indicator when the first side of the orientation calibration system is positioned along a side edge of the external monitor to display an indication from the orientation sensor of the present left/right orientation of the orientation calibration system and a desired left/right orientation of the external monitor, wherein the left/right graphical indicator changes as the left/right orientation of the external monitor is adjusted while the first side of the orientation calibration system is positioned along the side edge of the external monitor and the present left/right orientation of the orientation calibration system changes. The one or more processors of the orientation calibration system may be further configured to display an up/down graphical indicator when the back side of the orientation calibration system is positioned along the front surface of the external monitor to display an indication from the orientation sensor of the present up/down orientation of the orientation calibration system and a desired up/down orientation of the external monitor, wherein the up/down graphical indicator changes as the up/down orientation of the external monitor is adjusted while the back side of the orientation calibration system is positioned along the front surface of the external monitor and the present up/down orientation of the orientation calibration system changes.

In one specific aspect, the display screen of the orientation calibration system may be further configured to display a graphical representation of the present orientation when the orientation calibration system is aligned or abutted with an imaging source providing the target image so as to place the imaging source at a desired orientation.

In another specific aspect, the indication or notification of the present orientation may be displayed on the display screen using a graphical element, which may be referred to as a dynamic graphical element showing a tilt of the medical alignment device along one, two, or, in some embodiments, three axis.

In some embodiments, the dynamic graphical element includes a circle movable in a curved track, wherein the circle changes color when the difference between the present orientation of the medical alignment device and the reference orientation of the medical alignment device is within the threshold.

In other embodiments, the processor of the orientation calibration system may be configured to capture the reference image upon receiving a command from a user in response to the circle changing color. In some other embodiments, the dynamic graphical element may include a circle movable in a track or a gauge about a center position of the track or gauge, and wherein a notification is generated when the circle is within a predetermined range of the center position.

In yet some other embodiments, the processor may be configured to capture the reference image upon receiving a command from a user in response to the circle reaching the predetermined range of the center position.

In some other embodiments, the processor may be configured to capture the reference image automatically in response to the circle reaching the predetermined range of the center position.

In certain other embodiments, the orientation calibration system may elicit notifications when certain alignment or orientation of the orientation calibration system are achieved, and these notifications may be any known or available visual, graphical, auditory, and/or tactile notifications.

In another specific aspect, the orientation sensor may include at least one of a gyroscope, an accelerometer, and an inertial measurement unit.

In another general aspect, a method is disclosed for orienting a system for capture of a target image. The method may include determining a present orientation of the system using an orientation sensor, displaying a graphical representation of at least a portion of the present orientation of the system on a display screen of the system, capturing the target image from an imaging source using a camera of the system when a difference between at least a portion of the present orientation of the system and a reference orientation of the system is within a threshold, and displaying the captured target image on the display screen.

In one specific aspect, the method further includes displaying a graphical representation of at least a portion of the reference orientation of the system on the display screen along with the at least a portion of the present orientation of the system that indicates a difference between the at least a portion of the reference orientation and the at least a portion of the present orientation.

In another specific aspect, the method further includes receiving a request to capture the target image. Another aspect may include that the image is not captured until after receiving the request to capture the target image, and after the difference between the at least the portion of the present orientation of the system and the reference orientation of the system is within the threshold.

In yet another aspect, the method further includes generating a notification when the difference between at least a portion of the present orientation of the system and the reference orientation of the system is within the threshold. Another aspect may include that the notification may include one or more from the group that includes a visual notification, an auditory notification, a tactile notification, and a change in color notification.

In yet another aspect, the method may include that the captured target image also includes at least a portion of a graphical representation of the difference between the at least a portion of the reference orientation and the at least a portion of the present orientation.

In yet another general aspect, a method is disclosed for using an orientation calibration system to align a display monitor in an orthogonal position relative to the ground, and the display monitor having four sides with each adjacent side being orthogonal to one another and configured to display a target image. The disclosed method may include positioning a first side of the orientation calibration system adjacent a first side of the display monitor, determining the alignment of the first side of the display monitor using the orientation calibration system, adjusting the alignment of the first side of the display monitor to ensure it is in an orthogonal position relative to the ground within an acceptable threshold as determined by the orientation calibration system, positioning a back side of the orientation calibration system adjacent a front surface of the display monitor, determining the alignment of the front surface of the display monitor using the orientation calibration system, and adjusting the alignment of the front surface of the display monitor to ensure it is in an orthogonal position relative to the ground within an acceptable threshold as determined by the orientation calibration system.

In one specific aspect of the method, the orientation calibration system displays a left/right graphical indicator when the first side of the orientation calibration system is positioned along the first side of the display monitor to display an indication of the present left/right orientation of the orientation calibration system and a desired left/right orientation of the display monitor, and the left/right graphical indicator changes as the left/right orientation of the display monitor is adjusted while the first side of the orientation calibration system is positioned along the first side of the display monitor and the present left/right orientation of the orientation calibration system changes. Further, the orientation calibration system may display an up/down graphical indicator when the back side of the orientation calibration system is positioned along the front surface of the display monitor to display an indication from the orientation sensor of the present up/down orientation of the orientation calibration system and a desired up/down orientation of the display monitor, and the up/down graphical indicator changes as the up/down orientation of the display monitor is adjusted while the back side of the system is positioned along the front surface of the display monitor and the present up/down orientation of the orientation calibration system changes.

In another specific aspect, the method further includes capturing the target or reference image from an imaging source when a difference between the present orientation of the medical alignment device and the reference orientation of the medical alignment device is within a threshold. In some embodiments, capturing the target image or reference image from the imaging source when a difference between the present orientation of the medical alignment device and the reference orientation of the medical alignment device is within a threshold is automatically executed.

BRIEF DESCRIPTION OF THE DRAWINGS

For a more complete understanding of various embodiments of the present invention and the advantages thereof, reference is now made to the following brief description, taken in connection with the accompanying drawings, appendices, and detailed description, wherein like reference numerals represent like parts, and in which:

FIG. 4A illustrates a schematic side view of a medical operation system used in some embodiments for defining the sagittal angle of a pilot hole to be made in a vertebra;

FIG. 4B illustrates a schematic front view of a medical operation system used in some embodiments for defining the sagittal angle of a vertebra;

FIGS. 6A-6D illustrate example user interfaces for a computer-implemented program to perform the methods shown in FIGS. 5A-5D, wherein FIG. 6A illustrates an interface for selecting vertebra of a patient, FIG. 6B illustrates aligning the longitudinal axis of the apparatus with the sagittal plane, FIG. 6C illustrates defining a pedicle screw's position and its sagittal angle, and FIG. 6D illustrates generating an angle-indicative line for showing the angle between the longitudinal axis of the apparatus and the sagittal plane;

Like elements are indicated with like reference numerals.

DETAILED DESCRIPTION

Figure 1:
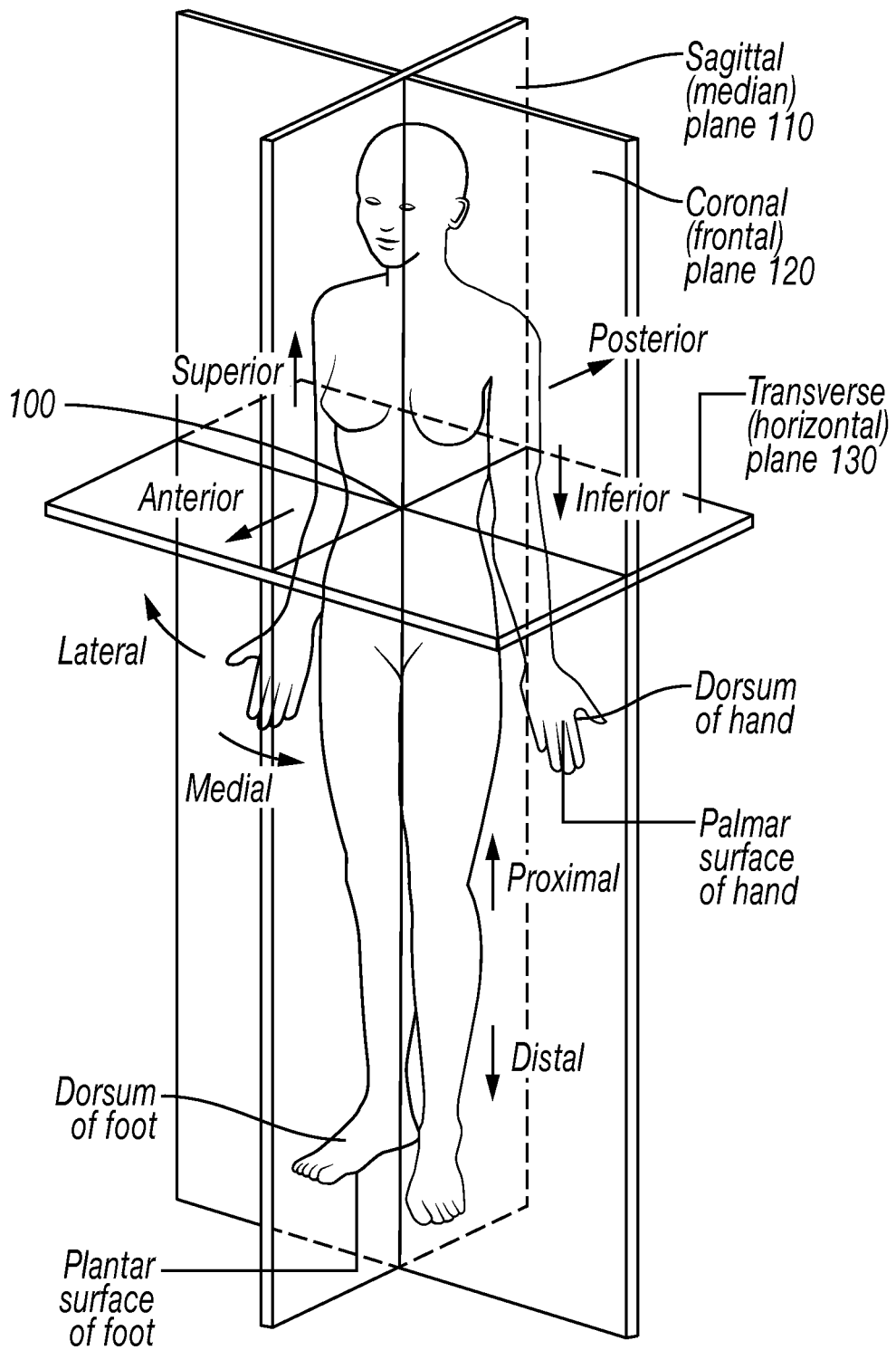
FIG. 1 illustrates definitions of a sagittal plane, a frontal plane, and a transverse plane relative to a patient's body.

In the following detailed description and the attached drawings and appendices, numerous specific details are set forth to provide a thorough understanding of the present disclosure. However, those skilled in the art will appreciate that the present disclosure may be practiced, in some instances, without such specific details. In other instances, well-known elements have been illustrated in schematic or block diagram form in order not to obscure the present disclosure in unnecessary detail. Additionally, for the most part, specific details, and the like, have been omitted inasmuch as such details are not considered necessary to obtain a complete understanding of the present disclosure, and are considered to be within the understanding of persons of ordinary skill in the relevant art.

It is further noted that, unless indicated otherwise, all functions described herein may be performed in hardware or as software instructions for enabling a computer, radio or other device to perform predetermined operations, where the software instructions are embodied on a computer readable storage medium, such as RAM, a hard drive, flash memory or other type of computer readable storage medium known to a person of ordinary skill in the art. In certain embodiments, the predetermined operations of the computer, radio or other device are performed by a processor such as a computer or an electronic data processor in accordance with code such as computer program code, software, firmware, and, in some embodiments, integrated circuitry that is coded to perform such functions. Furthermore, it should be understood that various operations described herein as being performed by a user may be operations manually performed by the user, or may be automated processes performed either with or without instruction provided by the user.

This disclosure describes an orientation calibration system for capturing a target image (also referred to as a reference image) and ensuring that the captured image is accurately captured, as well as methods of using and achieving the same. The orientation calibration system is illustrated herein in connection with FIGS. 1-18 as a medical alignment device operable to align a medical tool to a desired orientation relative to a patient (and a body part thereof). Although the current disclosure primarily describes orientation calibration system in connection with medical and diagnostic image applications, the orientation calibration system and related methods should not be understood to be limited to only medical type applications. On the contrary, such an orientation calibration system and related methods may be used for any of a variety of applications including, without limitation, for accurately capturing images at correct orientations, alignments, or angles for CAD drawings, construction drawings, maps, geology maps and formations, interior design, surgical navigation systems, three-dimensional printing applications, and the like.

The orientation calibration system enables an accurate measurement of relative orientation between the medical alignment device and the patient. For example, the medical alignment device simulates an insertion angle relative to a reference image, such as a CT scan or other scan of a bone of the patient. The orientation calibration avoids a mistaken reading of the relative angle as measured by the orientation sensor between the medical alignment device and the reference image, and thus enabling accurate subsequent alignment indications.

At a high level, the orientation calibration system is applicable to both the medical alignment device and an image provider, such as a display monitor showing or displaying a target image, such as a diagnostic image such as a CT or MRI scan. In one embodiment, the medical alignment device includes a display and an orientation sensor. The display shows a present orientation of the medical alignment device relative to a known reference frame, such as to a reference orientation. The reference orientation may be determined by aligning to a gravitational direction or the image provider, such as the monitor displaying an image. For example, the medical alignment device may be positioned and aligned to the image provider in the same plane. When capturing a copy of the reference image shown in the image provider, the medical alignment device can be oriented to be parallel to the image provider and have one longitudinal axis aligned with the gravitational direction (or forming a known angle relative to the gravitational direction). As such, the calibration enables the medical alignment device to ascertain subsequent increments of orientation to provide accurate readings.

FIG. 1 illustrates a sagittal or median plane 110, a frontal or coronal plane 120, and a horizontal or transverse plane 130 relative to a patient's body part 100 located at the intersection of the sagittal plane 110, the coronal plane 120, and the transverse plane 130. Each plane is orthogonal to each other such that if the position or orientation of an object, device, or medical hardware, such as a pedicle screw, is known in two of the orthogonal planes, the three-dimensional orientation angle of such item may be calculated or known. When discussing a vertebra (or other body parts) in the following disclosure, reference is made to the sagittal plane, coronal plane, and transverse plane. It should be understood that, when these planes are mentioned, they are not intended as a reference only to the specific sagittal, coronal, and transverse planes illustrated in FIG. 1, but rather, are intended as a reference to illustrate an orientation or location relative to the specific vertebra or body part being discussed.

Figure 2A:
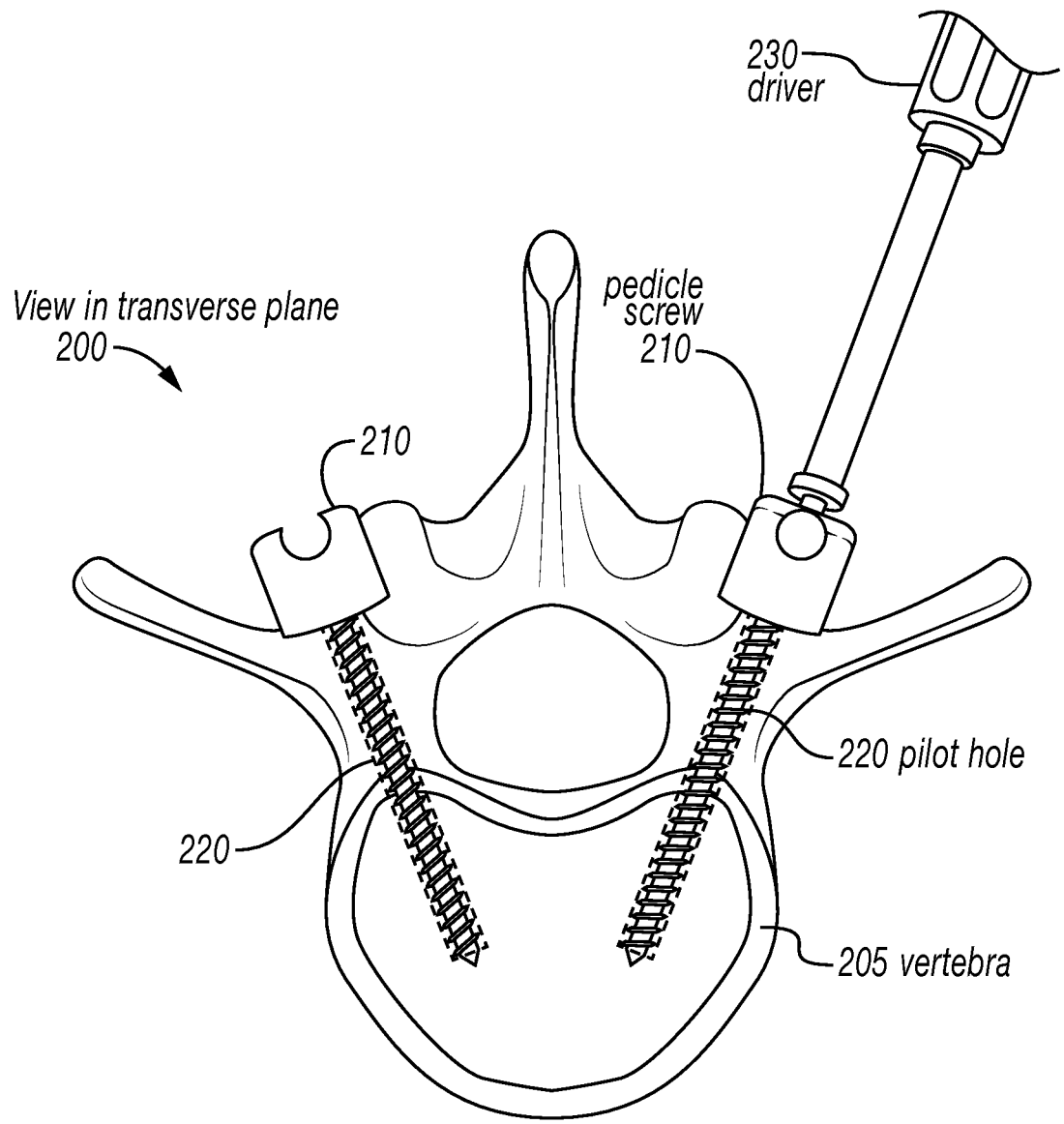
FIG. 2A illustrates a cross-sectional, axial view of a vertebra having pedicle screws installed in respective pilot holes.
Figure 2B:
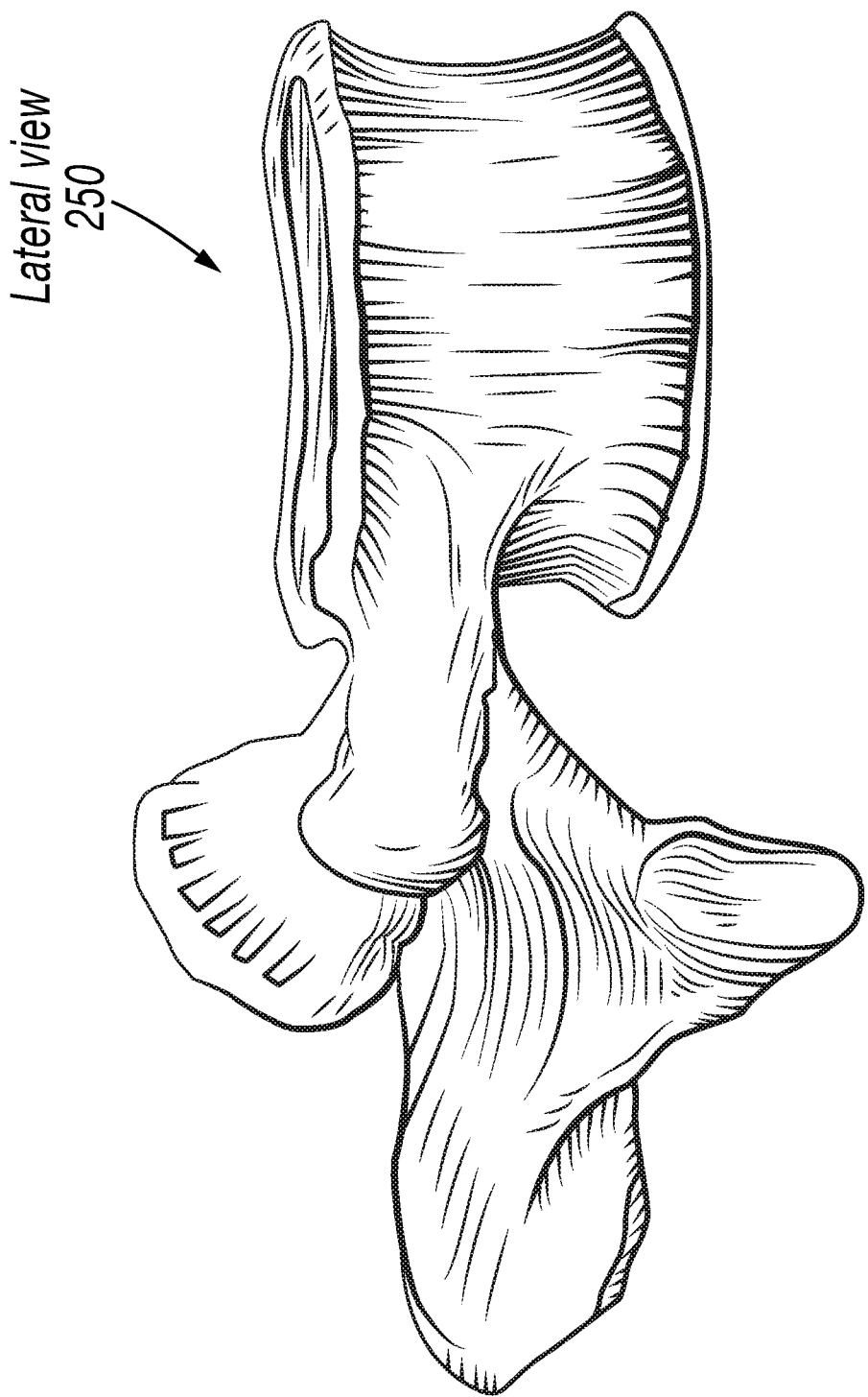
FIG. 2B illustrates an example lateral view of a vertebra for installing pedicle screws.
Figure 2C:
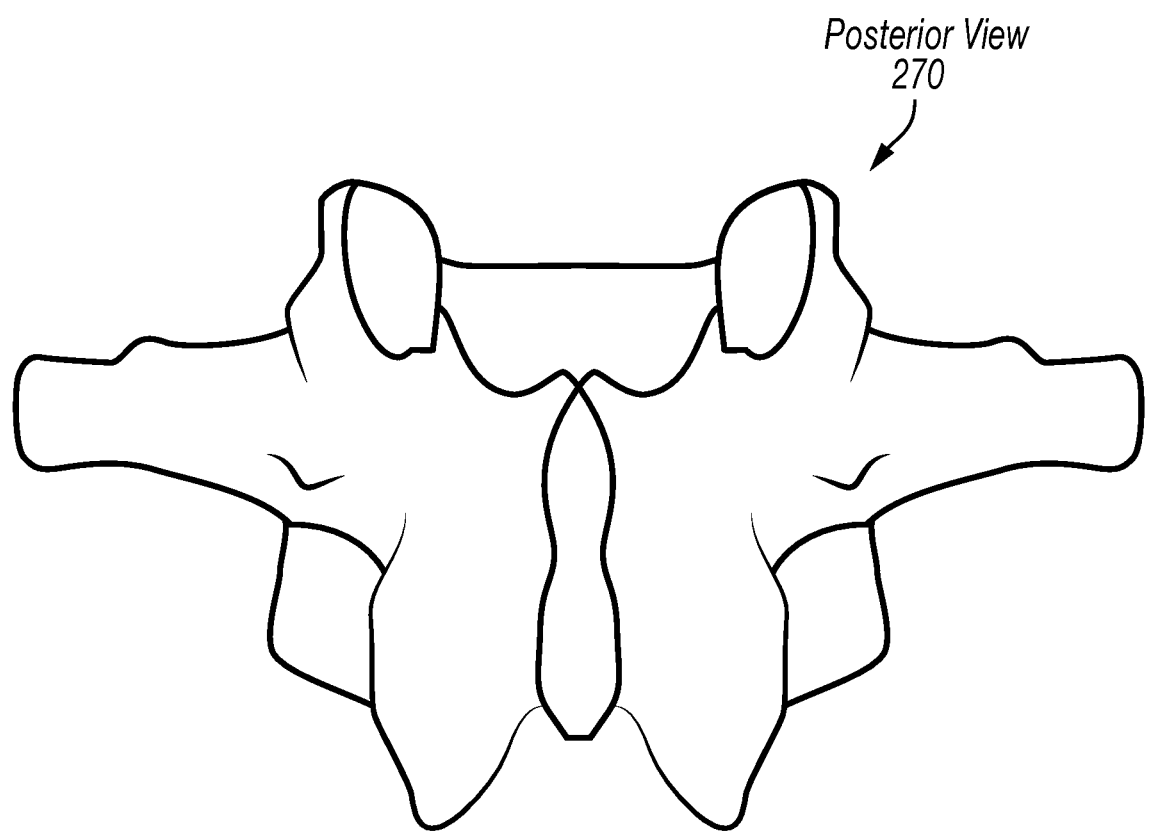
FIG. 2C illustrates an example posterior view of a vertebra for installing pedicle screws.

FIG. 2A illustrates a cross-sectional, axial view (may be referred to as a superior view) 200 of a vertebra 205 having pedicle screws 210 installed in respective pilot holes 220. A driver 230 may be used to screw the pedicle screws 210 positioned in pilot holes 220. Various shapes and types of pedicle screws 210 and driver 230 may be used. The pedicle screws 210 and driver 230 shown in FIG. 2A are for illustrative purpose only. A mating portion 252 of the driver 230, which may be referred to as a tool or a medical tool, may be provided to allow a medical alignment device in an attachment apparatus to "mate" or position adjacent such mating portion 252 to ensure that the driver 230 is installing the pedicle screw at a desired alignment angle, such as a three-dimensional alignment angle. FIG. 2B illustrates a lateral view (i.e., side view) 250 of a vertebra, which could be an orthogonal view of the vertebra 205 of FIG. 2A. FIG. 2C illustrates a posterior view 270 of a vertebra. The following discussion focuses on properly creating the pilot holes with a tool guided by the present disclosure.

Figure 3A:
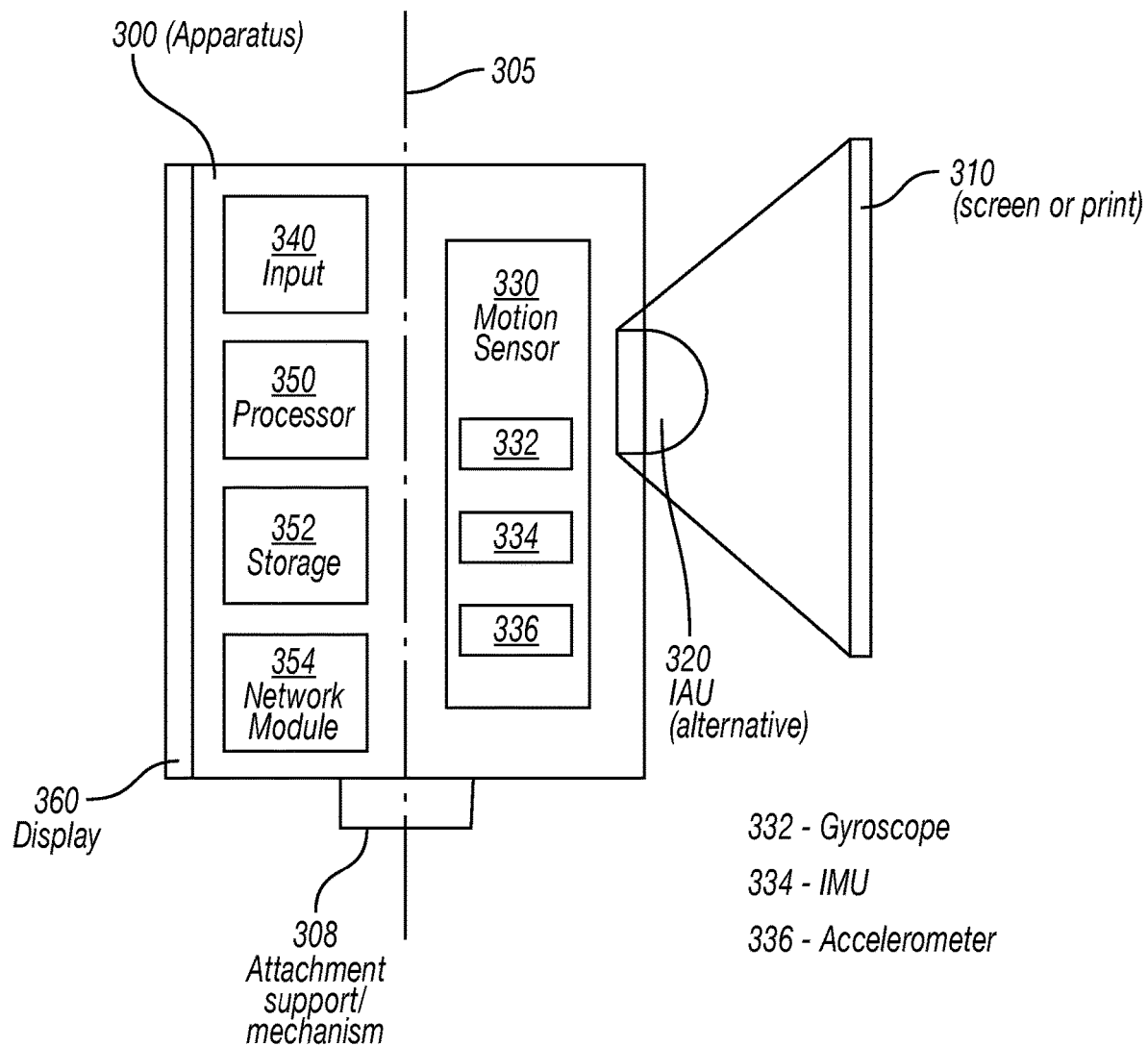
FIG. 3A presents a schematic diagram of an apparatus, which may be referred to as a medical alignment device, used in accordance with an embodiment to define and verify a three-dimensional alignment angle, which may also be referred to as an insertion angle, for use in installing devices, objects, hardware, and the like at a desired alignment angle.

FIG. 3A presents a schematic diagram of an apparatus 300, which may be referred to as a medical alignment device or alignment device, used in accordance with an embodiment to define and verify an angle, such as a three-dimensional alignment angle, for use in installing devices, objects, hardware, and the like, such as to align a pilot hole, or tract, such as the pilot hole 220 of FIG. 2. The apparatus 300 has an axis 305 (such as, for example, a longitudinal axis) that is used in some embodiments to align the apparatus 300 for image capture. The apparatus 300 includes an image acquisition unit 320 (or camera) for capturing an image 310 of the vertebra. In some embodiments, the image 310 may be obtained by positioning the apparatus 300 and/or image acquisition unit 320 in parallel with the transverse, sagittal, or coronal plane to obtain an image of the vertebra. These images may be diagnostic images such as, for example, CT scans, MRI scans, X-rays, and the like of items of interest, such as a vertebra. In some implementations, an attachment support and/or mechanism 308 is used to align and/or secure the apparatus 300 to a tool that creates a pilot hole for example.

In some embodiments, the image acquisition unit 320 can be a camera having sufficient field of view 360 to properly align the axis 305 of the apparatus 300 with a desired plane. In some embodiments, the axis 305 is representative of a vertical line centered laterally with respect to the image being captured. For example, if the desired image is intended to capture the vertebra from a cross sectional, axial view (e.g., see FIG. 2A), the axis 305 is aligned with the sagittal plane (i.e., the plane that is sagittal to the vertebra) and the image acquisition unit 320 is positioned parallel to the transverse plane to capture the top-down view of the vertebra shown in FIG. 2A. If the desired image is intended to capture the vertebra from a side view (e.g., a lateral image of the vertebra, see FIG. 2B), the axis 305 is aligned with the transverse plane (i.e., the plane that is transverse to the vertebra) and the image acquisition unit 320 is positioned parallel to the sagittal plane. If the desired image is intended to capture the vertebra from a posterior or anterior view (see, for example, FIG. 2C), the axis 305 is aligned with the sagittal plane and the image acquisition unit 320 is positioned parallel to the coronal plane.

In some embodiments, the image 310 may be a processed diagnostic image, e.g., an image displayed on a screen, a film, or a printed photograph. In other embodiments, the image acquisition unit 320 can directly use an image taken from an external machine (not illustrated), such as a radiograph, computed tomography (CT) scanner, or a magnetic resonance imaging (MRI) machine.

The orientation apparatus 330 is operable to detect changes in movement, orientation, and position. In some embodiments, the orientation apparatus 330 includes at least one of a gyroscope 332, an inertial measurement unit 334, and an accelerometer 336, in other embodiments it may only include the gyroscope 332 with three axes of rotation to be able to determine a three-dimensional orientation of the apparatus 300. The gyroscope 332 is operable to measure at least one axis of rotation, for example, the axis parallel to the intersection of the sagittal plane and the coronal plane. In other embodiments, the gyroscope 332 includes more than one sensing axes of rotation, such as three axes of rotation, for detecting orientation and changes in orientation. The inertial measurement unit 334 can detect changes of position in one or more directions in, for example, a cardinal coordinate system. The accelerometer 336 can detect changes of speeds in one or more directions in, for example, a cardinal coordinate system. In some embodiments, data from all components of the orientation apparatus 330 are used to calculate the continuous, dynamic changes in orientation and position.

The apparatus 300 further includes, in some embodiments, an input component 340 that is operable to receive user input, such as through a keypad or touchscreen, to receive a device, such as a pedicle screw to be installed in a vertebra, insertion location and the desired angle representing an insertion direction of the pedicle screw. An example illustration of the user input component 340 is presented in accordance with FIGS. 6A-6D, as well as FIGS. 12, 13A, 13B, and 18. In some embodiments, the input component 340 can include a multi-touch screen, a computer mouse, a keyboard, a touch sensitive pad, or any other input device.

In some embodiments, the apparatus 300 further includes a processor 350. The processor 350 can be any processing unit capable of basic computation and capable of executing a program, software, firmware, or any application commonly known in the art of computer science. As to be explained, the processor 350 is operable to generate a three-dimensional alignment angle based on alignment inputs from to views orthogonal to one another, and to output an angle-indicative line representing the orientation of a device, such as a pedicle screw, pilot hole, etc. on the display showing a diagnostic image where the device, such as a pedicle screw, is to be installed. In some embodiments, the angle-indicative line provides a notation that the orientation of the apparatus 300 approximately forms the desired angle. The angle-indicative line is not limited to showing sagittal angles, but also angles in different planes, such as, for example, the coronal plane or the transverse plane.

The apparatus 300 may, in some embodiments, further include a memory storage unit 352 and network module 354. The memory storage unit 352 can be a hard drive, random access memory, solid-state memory, flash memory, or any other storage device. Memory storage unit 352 saves data related to at least an operating system, application, and patient profiles. The network module 354 allows the apparatus 300 to communicate with external equipment as well as communication networks.

In some embodiments, the apparatus 300 further includes a display 360. In some embodiments, the display 360 is a liquid crystal display that also serves as an input using a multi-touch screen. In some embodiments, the display 360 shows the angle-indicative line to a user and provides a notification when the apparatus is approximately aligned with the predefined desired angle, as determined by the gyroscope 332 or the orientation apparatus 330. For example, the notification can include a highlighted line that notifies the user the axis 305 has reached the desired angle, or is within an acceptable range of the desired angle. The apparatus 300 may provide any number of notifications to a user, including visual, auditory, and tactile, such as, for example, vibrations. The apparatus 300 will include a speaker as well as a device to impart vibrations to a user to alert or notify a user.

Figure 7:
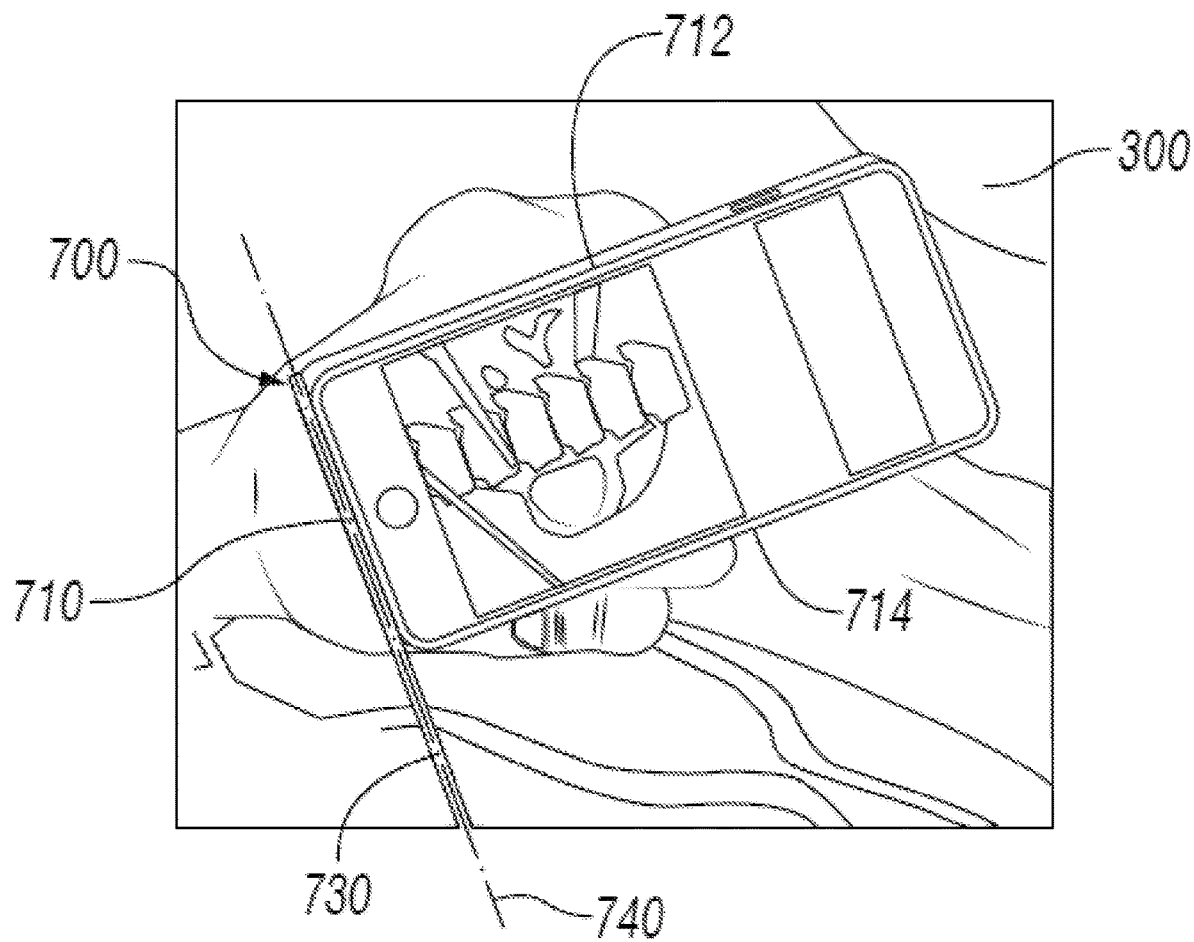
FIG. 7 illustrates an example of aligning the apparatus or medical alignment device.

Referring briefly to FIG. 7, in some implementations, the apparatus 300 (i.e., the medical alignment device) further includes an attachment support or mechanism 700 (also 308 of FIG. 3A) that allows the medical alignment device or apparatus 300 to be attached or provided adjacent to a tool, medical hardware, or equipment (i.e. a medical tool 730). The attachment apparatus 700 may be made of plastic, stainless steel, titanium, or any other material. The attachment apparatus 700 couples to the medical alignment device or apparatus 300 to the tool 730 by, for example, providing a casing that is attached to the medical alignment device 300 and is configured to connect to or abut the medical tool 730, for example, by aligning a first surface 710 of the medical alignment device 300 to the attachment apparatus 700 and thus to the medical tool 730. For example, the attachment apparatus 700 may be aligned to a longitudinal axis 740 of the medical tool 730. As such, orientation sensors in the medical alignment device 300 are properly aligned with the longitudinal axis 740.

In other implementations, a second surface 712 and a third surface 714 of the medical alignment device 300 may be used to secure and/or align the medical alignment device 300 to the attachment apparatus 700. In some embodiments, the attachment apparatus 700 may include a magnetic attachment apparatus for coupling the medical alignment device 300 to the tool 730 or to the attachment apparatus 700. The attachment apparatus 700 allows the medical alignment device 300 to provide real-time measurement and display of the orientation of the attached or aligned medical tool 730.

Returning to FIG. 3B, a schematic diagram of an axial view of a vertebra defining an alignment or insertion angle for a pilot hole in the vertebra in this plane for insertion or installation of a pedicle screw is provided. This view or diagnostic image of the vertebra may be electronically transmitted to the medical alignment device 300, or the view or image may be captured from a monitor or display of a diagnostic image using the image acquisition unit 320 of the medical alignment device 300 (sometimes referred to as apparatus 300). A sagittal angle 370 may be defined for the pilot hole 220 in the vertebra 205 that starts at the initial position 375, which may be referred to as the insertion location. The display 360 shows the field of view of the view captured by the image acquisition unit 320, assuming that was how the image was acquired, and allows a user to align the axis 305 of the apparatus 300 with the desired plane (e.g., the sagittal plane). In the embodiment shown in FIG. 3B, the sagittal angle 370 is the angle between the central axis 365 of the pilot hole 220 and the sagittal plane.

Figure 3B:
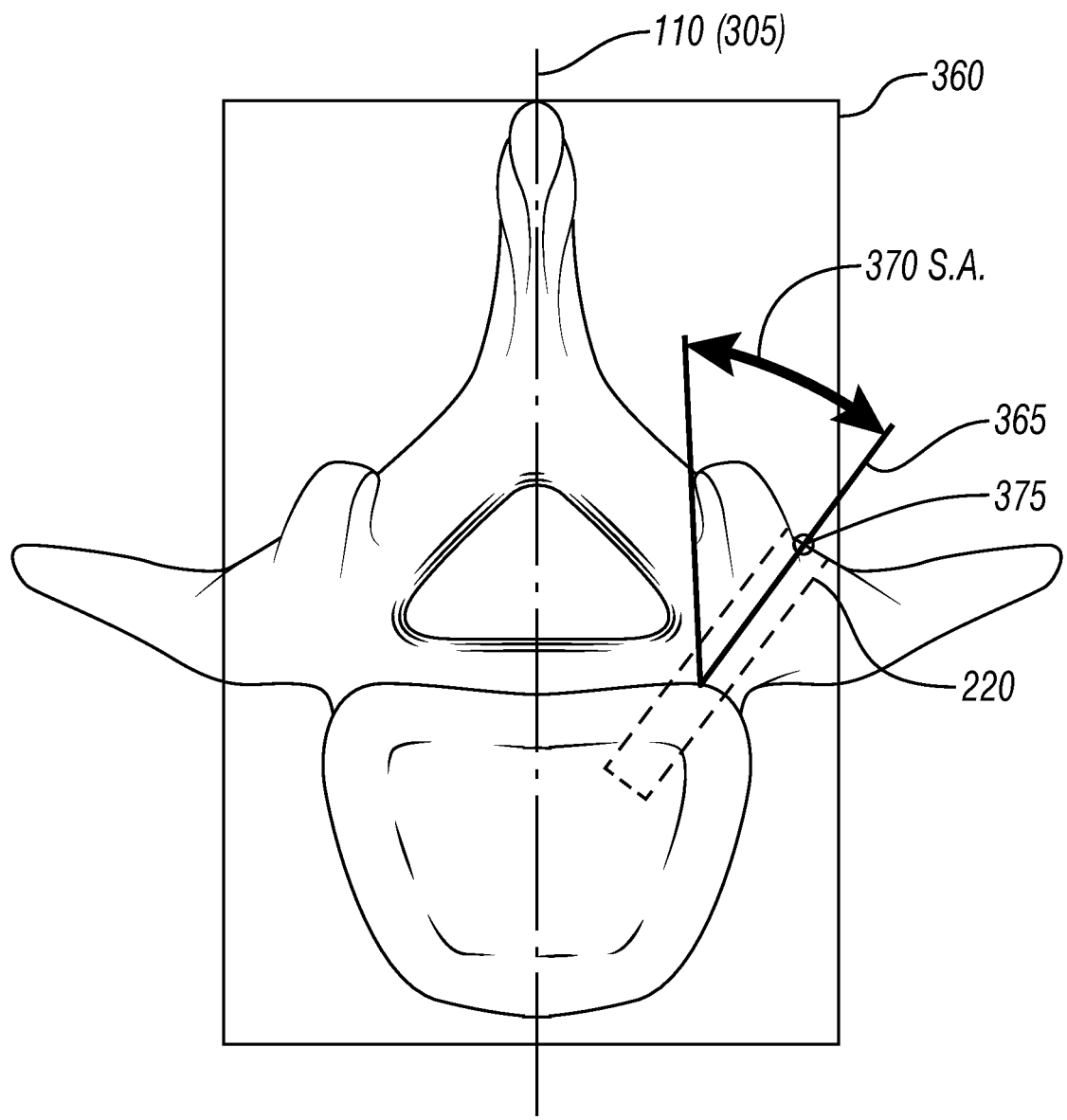
FIG. 3B illustrates a schematic diagram of an axial view of a vertebra for defining an alignment or insertion angle for a pilot hole in the vertebra in this plane.

FIG. 4A illustrates a schematic side view of a medical operation system 400 used in some embodiments for defining the sagittal angle 370 of a pilot hole to be made in a vertebra which may be used in some embodiments for defining the sagittal angle 370 of the vertebra shown in FIGS. 3A and 3B. The medical operation system 400 includes a machine 410 for capturing a cross-sectional view of the vertebra 205. The machine 410 may be, for example, a CT scanner or Mill machine. The patient exits the machine 410 after the image is taken, as shown in FIG. 4B.

FIG. 4B illustrates a schematic front view 450 of the medical operation system 400 taken in the transverse plane for defining the sagittal angle 370 of the vertebra 205. The front view axis 460 (and correspondingly, the side view axis 470) of the pilot hole should to be precisely defined for the drilling guide 455. In some embodiments, the apparatus 300 may be attached to the drilling guide 455 with the attachment support/mechanism 308. Defining and verifying the sagittal angle 370 may be performed at the apparatus 300, as explained in connection with the method illustrated in FIG. 5B.

Figure 5A:
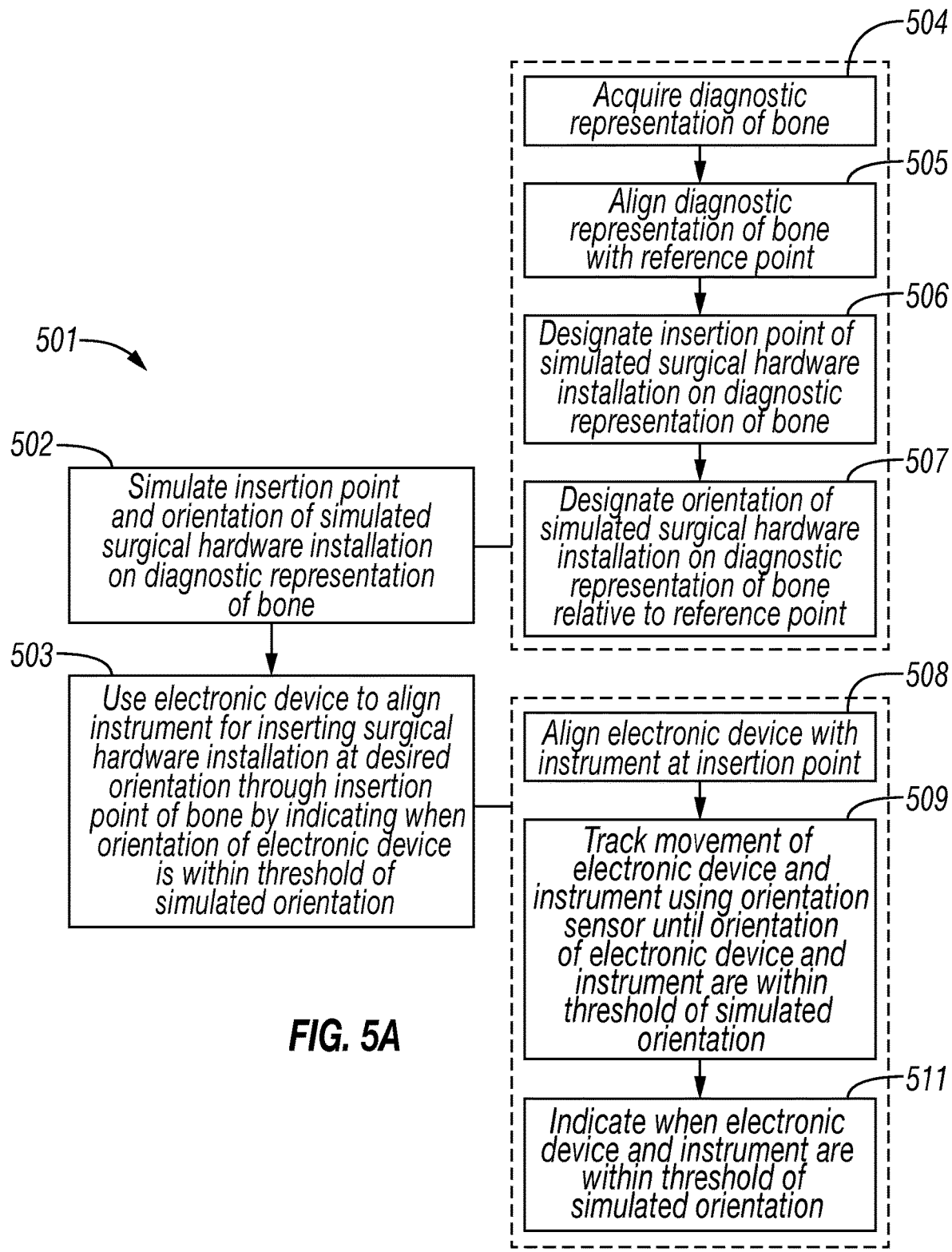
FIG. 5A illustrates an example flowchart for a method of determining an orientation of an instrument for inserting a medical device in a bone, in accordance with one or more embodiments of the present disclosure.

First, however, an example method of determining an orientation of an instrument for inserting a medical device in a bone is now described with reference to the flowchart 501 of FIG. 5A. A diagnostic image is obtained at the apparatus 300 and displayed. An insertion point and a desired orientation of a simulated surgical hardware installation are simulated and displayed on a diagnostic representation of a bone at block 502 and the desired alignment orientation is stored. Proceeding to block 503, the apparatus or medical alignment device 300 with orientation sensor, such as gyroscope 332, is used to align a tool, such as a medical tool, drill or the like for inserting or installing the surgical hardware at the desired alignment orientation from block 502 and through the insertion point of the bone by indicating when an orientation of the medical alignment device 300 is within a threshold of the simulated orientation with the desired alignment angle.

Simulating the insertion point and the orientation of the simulated surgical hardware installation on the diagnostic representation of the bone includes acquiring the diagnostic representation of the bone at block 504, aligning the diagnostic representation of the bone with a reference point at block 505, designating the insertion point of the simulated surgical hardware installation on the diagnostic representation of the bone at block 506, and designating the orientation of the simulated surgical hardware installation on the diagnostic representation of the bone relative to the reference point at block 507.

If block 502 is repeated using a second diagnostic representation of the bone that is orthogonal to the first diagnostic representation, the same steps 504 through 507 may be repeated on the second diagnostic representation with the location of the simulated surgical hardware constrained to the selections or settings made when the insertion point and orientation were selected in the first diagnostic representation. Once this is done, a three-dimensional alignment angle may be calculated or determined. This may be done by the apparatus or medical alignment device 300.

Using the electronic device, which may be the apparatus or medical alignment device 300, to align the instrument or tool for inserting the surgical hardware installation at the desired orientation through the insertion point includes aligning the electronic device with the instrument or tool at the insertion point in block 508, tracking movement or orientation of the electronic device and the instrument or tool using an orientation sensor, such as gyroscope 332, of the electronic device until the orientation of the electronic device and the instrument are within the threshold of the simulated orientation at block 509, and indicating when the electronic device and the instrument are within the threshold of the simulated orientation at block 511. The indication may be visual, auditory, or tactile. The orientation of the electronic device, and hence the alignment of the instrument or tool, may be a two-dimensional alignment angle, in certain implementations, or a three-dimensional alignment angle. FIG. 7 illustrates an example application of the alignment of block 508.

Figure 5B:
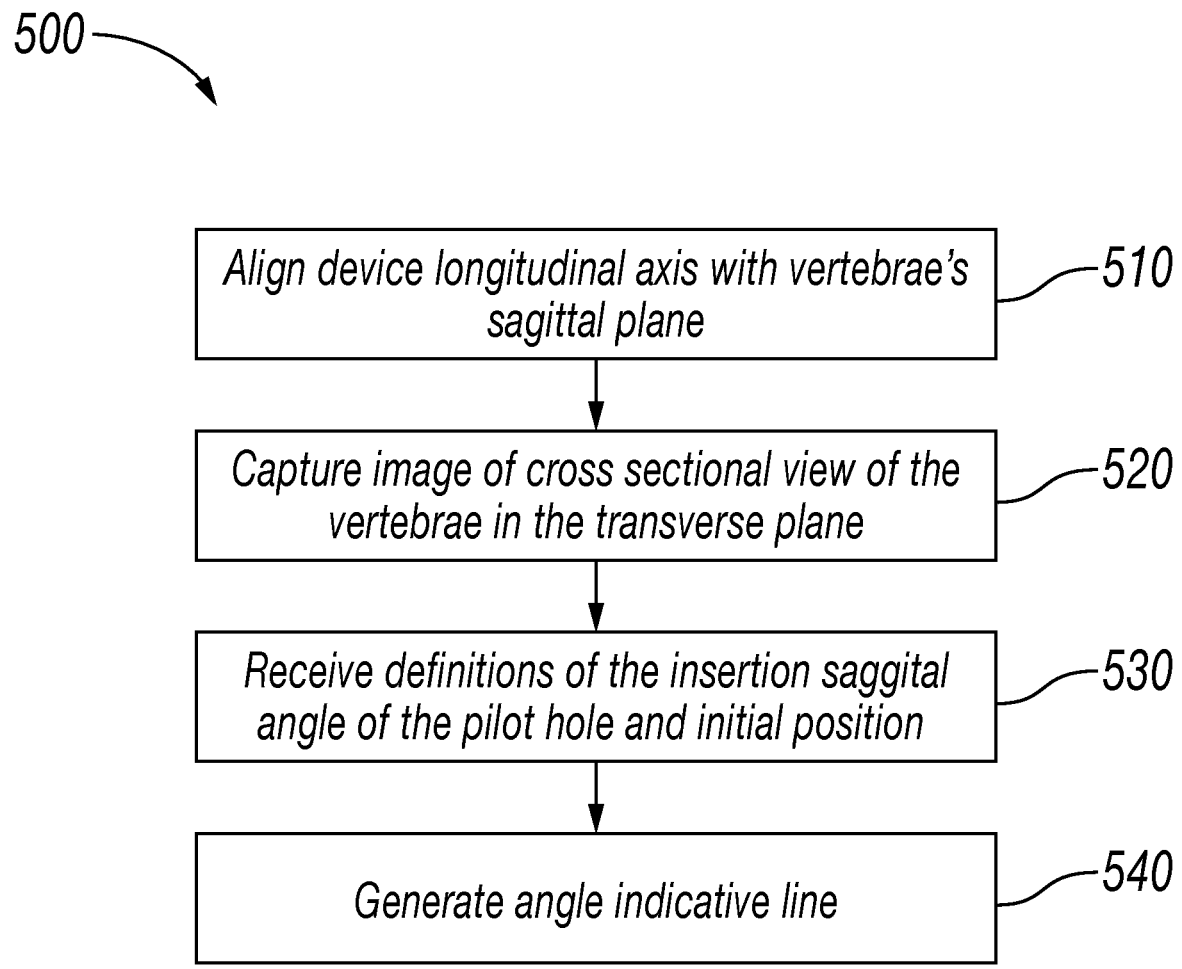
FIGS. 5B, 5C, and 5D illustrate example flowcharts for methods for indicating the sagittal angle, transverse angle, and coronal angle, respectively, in accordance with one or more embodiments of the present disclosure.
Figure 5C:
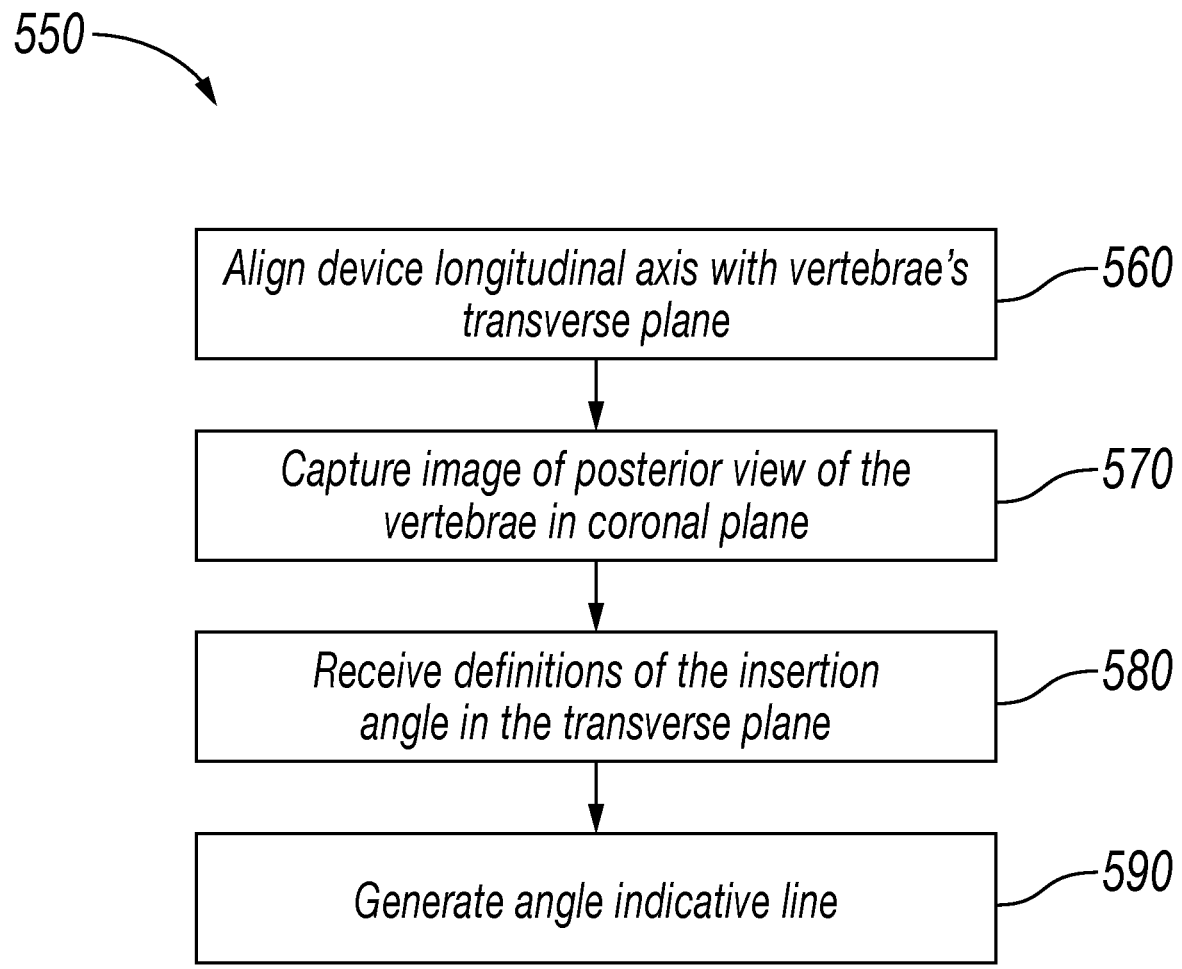
Figure 5D:
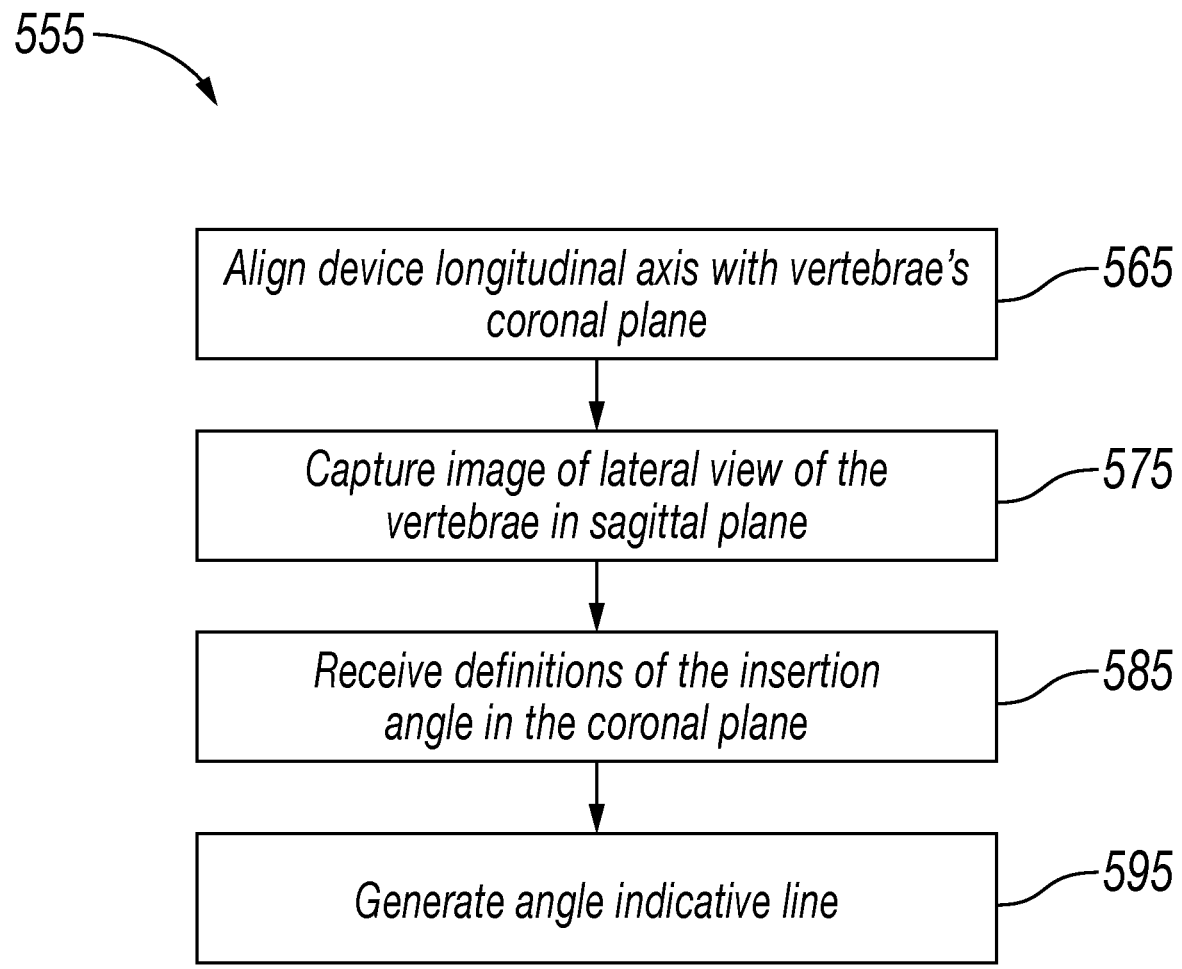

FIGS. 5B, 5C, and 5D illustrate example flowcharts for methods for indicating or determining a desired alignment angle, which also may be referred to as an insertion angle, in the: (i) sagittal plane, which may be referred to as the sagittal angle, (ii) the transverse plane, which may be referred to as the transverse angle, and (iii) the coronal plane, which may be referred to as the coronal angle, respectively, in accordance with one or more embodiments of the present disclosure. Each of these methods may be thought of as generating or determining a two-dimensional alignment angle in their respective plane.

FIG. 5B illustrates an example flowchart 500 of a method for indicating the sagittal angle 370. The method of the flowchart 500 is for verifying any insertion angle 370 of the pilot hole 220 in the sagittal plane 110 for receiving a pedicle screw 210 in the vertebra 205. At 510, the axis 305 of the apparatus 300 is aligned or is oriented with the sagittal plane of an image of the vertebra, in this embodiment. In some embodiments, a user may hold the apparatus 300 and rotate the apparatus 300 to match a marking indicating the axis 305 with features of the vertebra 205 that indicate the sagittal plane. In some embodiments, the marking may be displayed on the screen as the user aligns the device. In other embodiments, the image of the vertebra (or other desired object or bone) is a diagnostic image that is displayed on the apparatus 300, which may be a medical alignment device 300, and is already oriented in some manner to the sagittal plane.

At 520, the image of the cross-sectional view is captured in the transverse plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent or transmitted to the apparatus 300 via a wired or wireless connection to be displayed on the apparatus 300 such that no physical representation (e.g., films, photos, monitors) may be needed for this step.

At 530, definitions of the insertion sagittal angle 370 of the pilot hole 220 and the initial position 375, also referred to as the insertion location, of the pilot hole 220 are provided or specified by a user. This input operation may be performed using various input devices of the apparatus 300, including a computer mouse, a keyboard, a touchscreen, or the like. In one embodiment, a multi-touch screen (e.g., the display 360) is used for both displaying the image and receiving the definition input from a user. Example illustrations of this input are provided in FIGS. 6A-6D, where the insertion location or initial position 375 of the pilot hole 220 for the installation of a pedicle screw are established by locating (or simulating) graphically the insertion location on the displayed diagnostic image, and the applicable alignment angle for the displayed plane may defined by moving or locating (or simulating) the desired position of the alignment angle of the pilot hole/pedicle screw.

At 540, an angle-indicative line is generated by a processor and displayed on the display 360 along with the diagnostic image. The angle-indicative line can rotate in response to the apparatus 300 rotation and provides a notification when the orientation or position of the apparatus 300 approximately forms the insertion sagittal angle 370 between the apparatus 300 longitudinal axis 305 and the sagittal plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the orientation or position of apparatus 300 to generate the current orientation of the apparatus 300. This current orientation may be compared to the desired insertion angle (or alignment angle) discussed above in connection with 530 to determine whether or not alignment exists or the extent of alignment, and this may be compared or shown graphically.

The indicative line may generate notations in various forms, including a visual alert such as highlighting the angle-indicative line, an audio alert such as providing a continuous sound with variable frequency indicative of the proximity between the current angle and the desired angle, and a small vibration that allows the user to notice the angular change. It should be appreciated that any audio alert may be used, such as a single sound or series of sounds when the desired angle is reached. Likewise, a single vibration or a series of vibrations may be emitted when the desired angle is reached. In some implementations, the flowchart 500 illustrated in FIG. 5B may be applicable for generating indication angles in the transverse plane or the coronal plane for indicating a respective transverse angle or a coronal angle.

FIG. 5C illustrates a flowchart 550 of an implementation for indicating a transverse angle, which is an angle with respect to the transverse plane of the vertebra. The method of the flowchart 550 is for verifying any pedicle screw insertion angle in the transverse plane of the vertebra 205. At 560, the axis 305 of the apparatus 300 is aligned with the transverse plane. In some embodiments, a user may hold the apparatus 300 and rotate the apparatus 300 to match a marking indicating the axis 305 with features of the vertebra 205 that indicate the transverse plane. In some embodiments, the marking may be displayed on the screen as the user aligns the device.

At 570, an image of the posterior view is captured or provided in the coronal plane. In one embodiment, the apparatus 300 includes a smart phone, a tablet computer, a laptop computer, or any portable computational device including those that include a camera for capturing a representation of the cross-sectional view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 580, definitions of the insertion angle in the transverse plane 130, and the initial position 375 of the pilot hole are provided by a user, as similar to the sagittal angle defined at 530.

At 590, an angle-indicative line for the corresponding transverse angle is generated by a processor and displayed on the display 360. The angle-indicative line can rotate in response to the apparatus 300 rotation and provides a notification when the apparatus 300 approximately forms the insertion transverse angle, as defined in step 580, between the apparatus 300 longitudinal axis 305 and the transverse plane. In some implementations, the angle-indicative line is a rotating line generated in the display 360 that allows a user to constantly monitor the change of orientation of the apparatus 300. The orientation monitoring is performed with an orientation apparatus 330. More specifically, in some embodiments, a gyroscope 332 that includes at least one axis of rotation may provide the function of monitoring the orientation or position of the apparatus.

FIG. 5D illustrates a flowchart 555 of another implementation for indicating a coronal angle. The method of the flowchart 555 is for verifying any insertion angle of a pedicle screw 210 in the vertebra 205 in the coronal plane 120. At 565, the axis 305 of the apparatus 300 is aligned with the coronal plane. In some embodiments, a user may hold the apparatus 300 and rotate the apparatus 300 to match a marking indicating the axis 305 with features of the vertebra 205 that indicate the coronal plane. In some embodiments, the marking may be displayed on the screen as the user aligns the device.

At 575, the image of the lateral view is captured in the sagittal plane. In one embodiment, the apparatus 300 includes a smart phone, a tablet computer, a laptop computer, or any portable computational device including those that include a camera for capturing a representation of the posterior view of the vertebra 205. In other embodiments, the image of the vertebra 205 may be sent to the apparatus 300 via a wired or wireless connection to be displayed on the apparatus 300 such that no physical representation (e.g., films, photos, monitors) may be needed for this step.

At 585, respective definitions of the insertion angle in the coronal plane 120, and the initial position 375 of the pilot hole are provided by a user, as similar to the sagittal angle defined at 530.

At 595, an angle-indicative line for one of the corresponding coronal angle is generated by a processor and displayed on the display 360. The angle-indicative line can rotate in response to the apparatus 300 orientation and provides a notification when the apparatus 300 approximately forms the insertion coronal angle between the apparatus 300 longitudinal axis 305 and the coronal plane. In some implementations, the angle-indicative line is a rotating line generated in the display 360 that allows a user to monitor the change of orientation of the apparatus 300. The orientation monitoring is performed with an orientation apparatus 330 of the apparatus 300. More specifically, in some embodiments, a gyroscope 332 that includes at least one axis of rotation may provide the function of monitoring the apparatus's orientation or position.

Figure 6A:
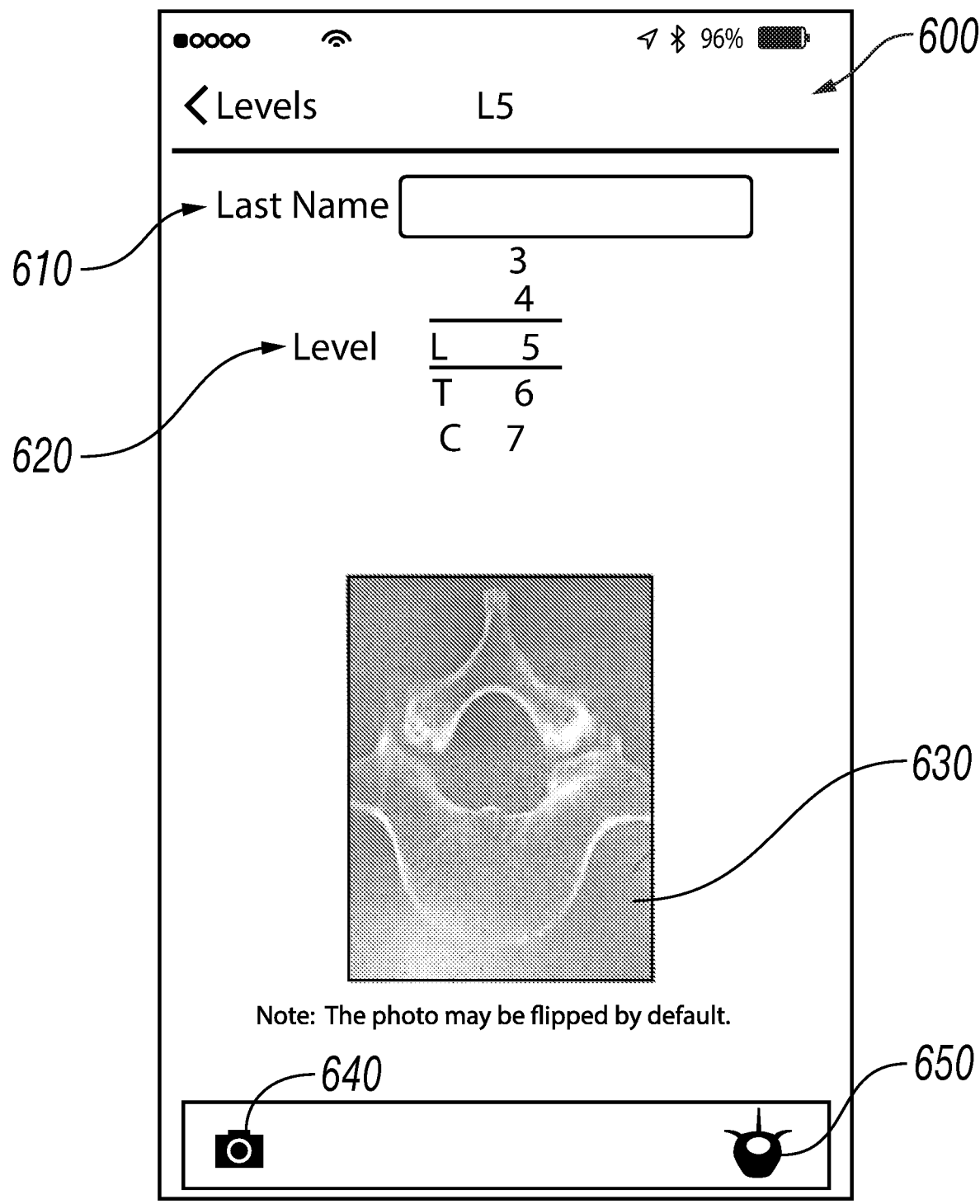
Figure 6B:
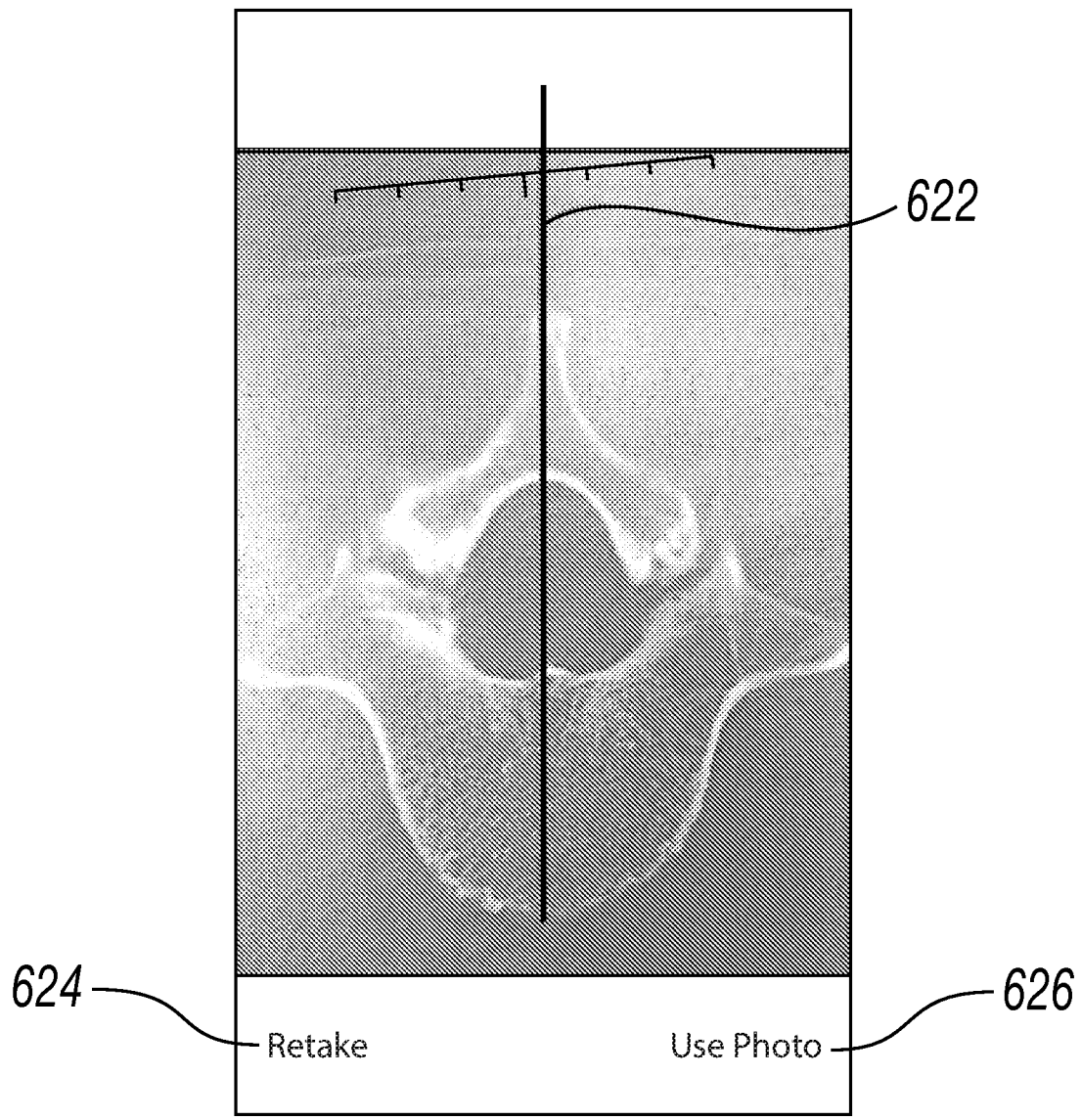
Figure 6C:
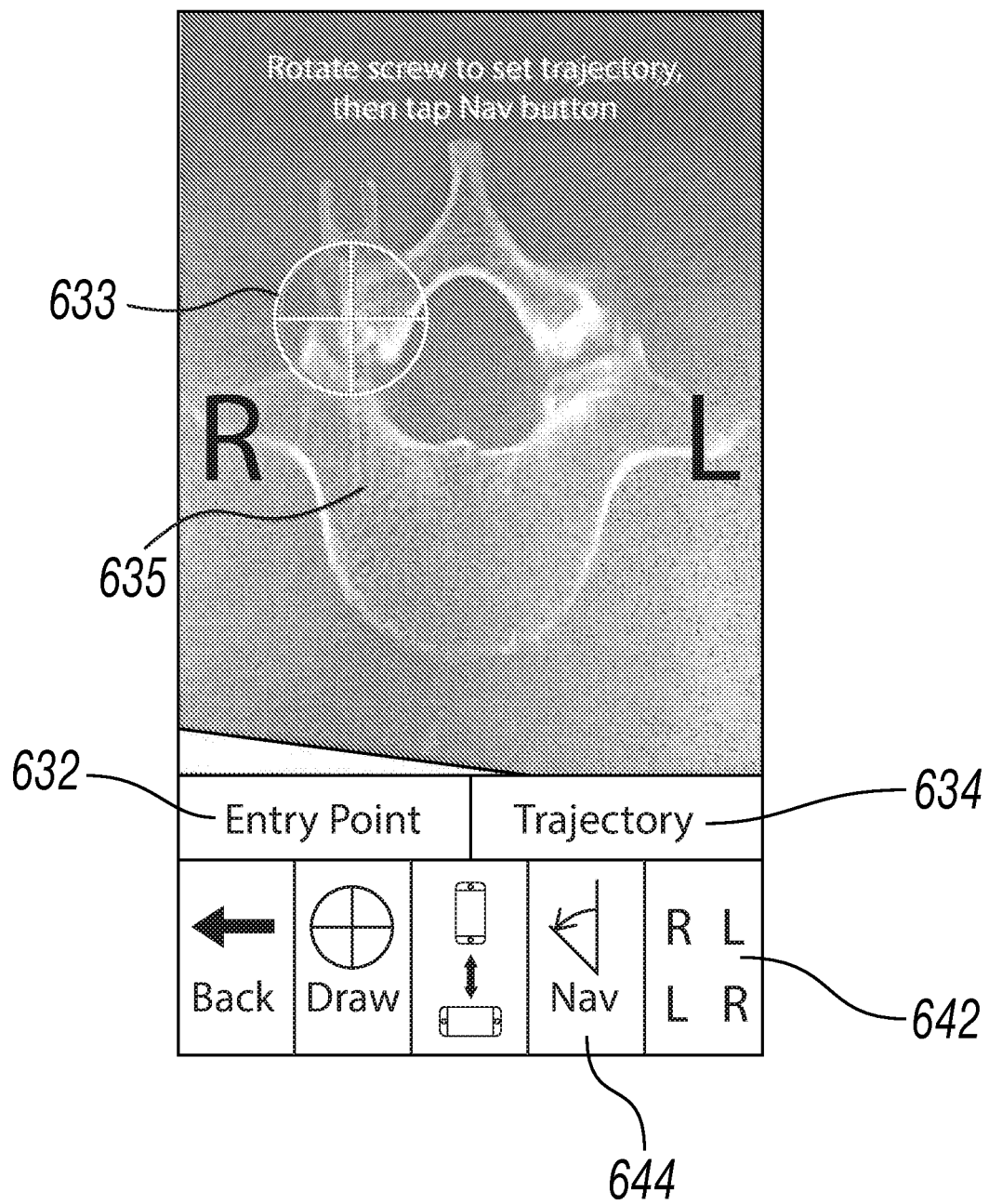
Figure 6D:
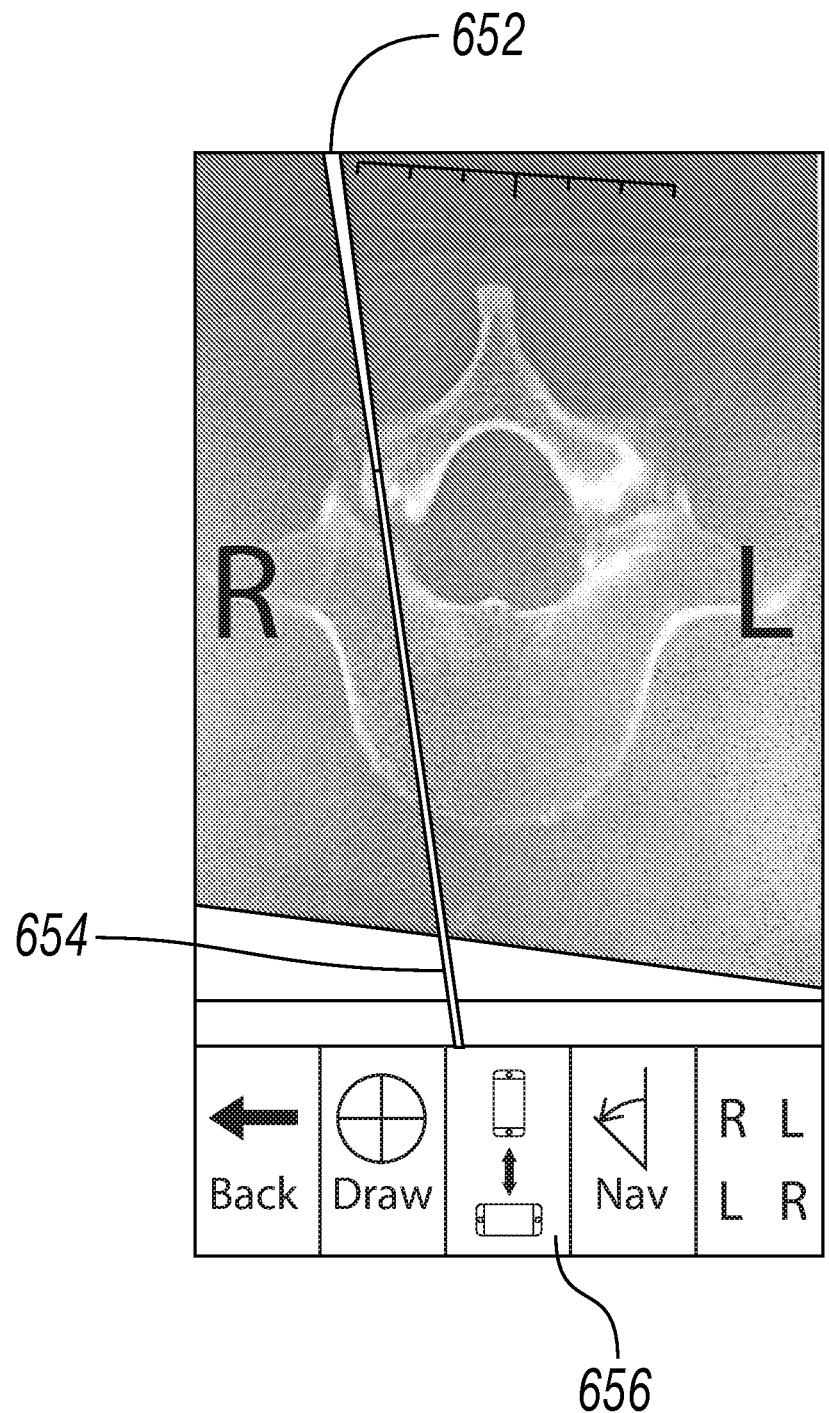

FIGS. 6A-6D illustrate examples of user interfaces for controlling a computer implemented program to perform the methods shown in FIG. 5A-5D. FIG. 6A illustrates an interface 600 for selecting vertebra of a patient, FIG. 6B illustrates displaying a diagnostic image and aligning (or confirming the alignment) the axis 305 of the apparatus 300 with the sagittal plane of the image, FIG. 6C illustrates defining a pedicle screw's position, including its insertion location or entry point at the cross hair, and its sagittal angle 370 on the diagnostic image, and FIG. 6D illustrates generating an angle-indicative line 652 for showing the angle between the longitudinal axis of the apparatus and the sagittal plane. In some embodiments, the angle-indicative line may represent a virtual gear shift pedicle probe, or other instrument for aligning a pedicle screw or pilot hole. When the virtual gear shift or angle is properly aligned, the virtual gear shift may change colors, or may change length or width. The angle-indicative line can rotate or reorient in response to the apparatus 300 rotation or reorientation, and provides a notification when the apparatus 300 approximately forms the desired alignment angle in this view between the apparatus 300 longitudinal axis 305 and the desired alignment angle.

In FIG. 6A, the patient's profile may be selected or added by typing the last name of the patient in the window 610. The corresponding vertebra for the desired angle is selected in the window 620. The camera button 640 allows a user to take a picture of a diagnostic image of the actual vertebra or to receive such a diagnostic image. The diagnostic image or picture is shown in the window 630. The button 650 allows the user to move onto the next step. As previously discussed, the picture at the vertebra may be provided without use of the camera or camera button 640.

For example, by using a camera of a mobile device, a user can take a picture of an axial view (either CT or MRI) in the transverse plane 130, of the desired vertebral body 205. Use the line 622 to line up the vertebral body so that it is proximately vertical for aligning with the sagittal plane (or other desired plane), as shown in FIG. 6B. A retake button 624 allows the user to go back to the previous steps to retake the image to ensure the alignment is proper. The button 626 allows the user to select the current photo to be used in the following operations.

After selecting button 626, the user may be returned to the detail view as shown in FIG. 6C. The photo may, in some embodiments, be automatically flipped to approximate its position during surgery. Button 642 may be selected to flip the orientation of the photo. For example, the RL button 642 can be used to flip the picture (and pedicle screw) depending on whether the surgeon is placing the screw while looking towards the patient's head (e.g., in the longitudinal axis toward the cephalad direction) or towards their feet (e.g., in the longitudinal axis toward the caudal or caudad direction).

The user next selects the optimal pedicle screw position by selecting the navigation button 644 to move the simulated pedicle screw to a desired location by moving the crosshairs 633 to the cortical entry point of the screw, for example, by tapping the entry point button 632 to confirm, and then tapping the trajectory button 634 and rotate the screw to its desired position 635. The crosshairs 633 specify the insertion location, such as the initial position 375 of FIG. 3B.

Tap the Nav button 644 and a virtual gear shift probe 652 (which may represent any tool or axis, such as a drill or pilot hole longitudinal axis) appears on the screen. The gear shift probe's orientation matches the orientation of the apparatus 300, which will include orientation circuitry, such as a gyroscope to determine the orientation of apparatus 300. In some embodiments, once the angle of the gear shift probe 652 is about 20 degrees within the selected trajectory, the gear shift probe 652 will turn yellow, at 5 degrees, it will turn green, and when the alignment is within 1 degree of the target angle, a green line 654 will extend outward and the pedicle screw will disappear to signify that the apparatus 300 is properly aligned.

In some embodiments, the device or apparatus 300 can be placed in a sterile bag and then be placed against the gear shift probe as it is being used to create the path for the pedicle screw. As provided herein, the apparatus 300 may be positioned in an attachment apparatus so that the apparatus 300 may be conveniently aligned or abuted with a tool, such as the gear shift probe, drill, and the like.

Some gear shift probes may be too short to allow the device (apparatus 300) to be placed against them lengthwise. If this is the case, tap the 90 degree button 656 and the screen will be rotated so the short edge of the device can be placed against the gear shift probe.

Other implementations of the disclosed system and method are possible. For example, the apparatus 300 may also use a second or more views to define various angles not limited within the sagittal plane. For example and in accordance with the foregoing disclosure, images of the vertebra may be captured from two orthogonal planes, such as through superior, lateral, posterior, anterior views, and various combinations thereof, to provide multiple reference points so that three-dimensional representations of the alignment angles can be presented.

In addition, different mobile computer devices may be used or modified into the apparatus 300 by equipping corresponding image acquisition units, input terminals, and motion or orientation sensing units. In some embodiments, the apparatus 300 includes a smart phone or another electronic device having a gyroscope. In addition, other motion or orientation sensors may be included such as the inertial measurement unit 334, and the accelerometers 336. The apparatus 300 may also be attached onto various medical devices or equipment for guiding insertion angles that require high precision and ease of use. The smartphone may be an iPhone for example. Also, in some application, the mobile computer device may be an iPod Touch, iPad, Android phone, Android tablet, Windows Phone, Windows tablet, or Blackberry phone. Also, in some applications, the mobile computer device may be an Apple TV in combination with an Apple TV remote, or a Nintendo Wii in combination with a Nintendo Wii remote. Indeed, the mobile computer device may be any combination of electronic devices where the orientation sensor (such as a gyroscope) is in one electronic device and the processor is in another electronic device.

In some embodiments, axis other than the device's longitudinal axis may be used. Axes can be defined by a portion of the device (e.g., an edge or surface of the device). More than one orientation apparatus 330 may be used at the same time, if desired. Surgical apparatus may include pedicle screws, gear shift probes, and other medical devices.

It should be appreciated that the various methods and techniques described above may be utilized with a virtual reality or augmented reality device, either on its own or in conjunction with another electronic device such as a smartphone or computer. The determination of the insertion point or pilot hole and the proper angle for the surgical tool used to attach or install the pedicle screw or other medical device may proceed in any of the fashions as described above, and then the virtual reality or augmented reality device may be used to display the proper insertion point or pilot hole and proper angle for the surgical tool to a physician.

In the case of a virtual reality device, the simulation of a tool or axis at a desired three-dimensional alignment angle or other alignment angle may be displayed to the surgeon or user in an immersive three-dimensional fashion so that the surgeon can view the bone or tools used in a procedure as it will appear during a surgery. In addition, the planning of the insertion point or pilot hole and the proper angle for the surgical tool may be conducted with the aid of the virtual reality device.

In the case of an augmented reality device, during the actual surgery, virtual visual indicia may be displayed superimposed over the real bone, illustrating to the physician precisely where to insert the surgical tool and at precisely which angle the surgical tool should be inserted and operated.

An augmented reality or virtual reality based system 700 for use in assisting of the determination of the proper insertion point and proper angle for a surgical tool to be used to install a pedicle screw is now described with reference to FIG. 8. The system 700 includes an electronic computing device 702, such as a smartphone, tablet, desktop based personal computer, or laptop based personal computer. A virtual reality based or augmented reality based device 704, such as a wearable headset, wearable goggles, three dimensional projector, or holoprojector, may be capable of wired or wireless communication with the electronic computing device 702.

Figure 9:
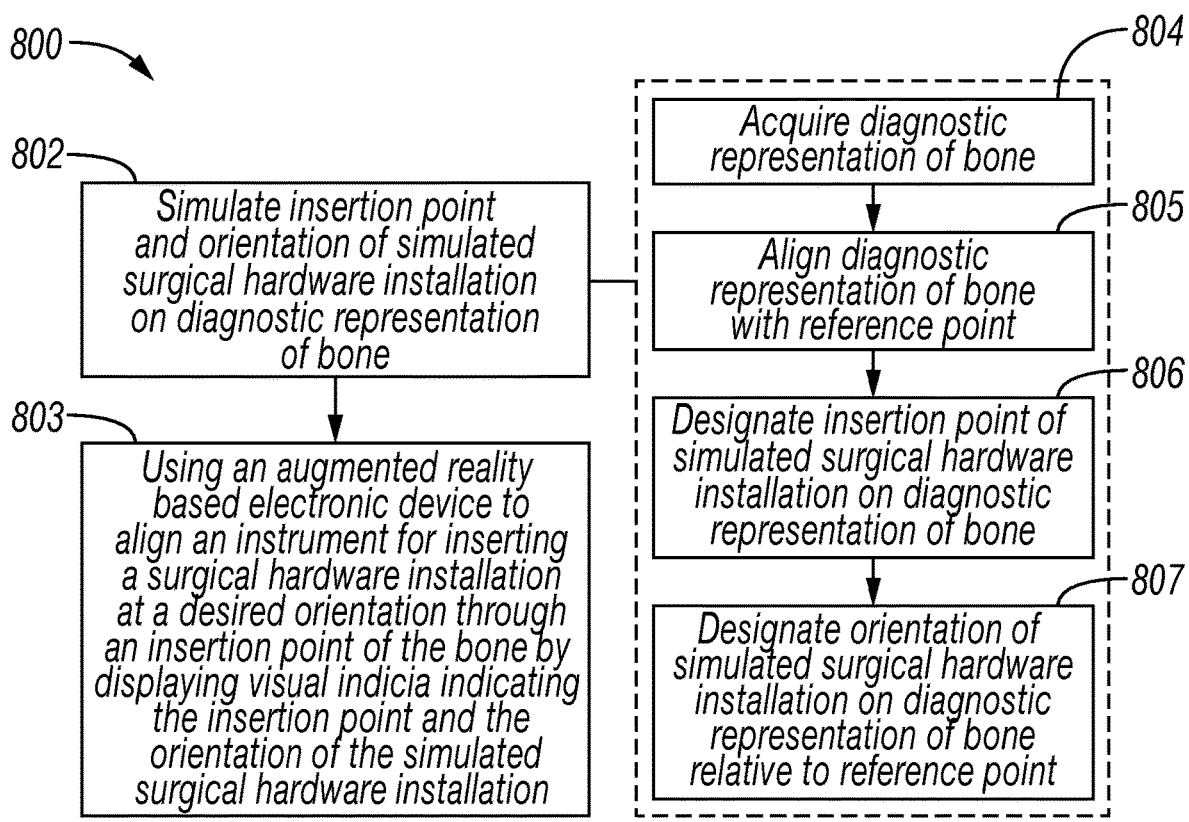
FIG. 9 illustrates an example flowchart for a method of determining and displaying an orientation of an instrument for inserting a medical device in a bone, using an augmented reality device, in accordance with one or more embodiments of the present disclosure.

Operation of the system 700 is now described with reference to the flowchart 800 shown in FIG. 9. Operation begins with the electronic computing device 702 simulating an insertion point and orientation of a surgical hardware installation on a diagnostic representation of the bone onto which it is to be installed (Block 802). This operation can proceed in any of the ways described above, although it should be understood that the virtual reality based or augmented reality based device 704 may be used as a display during this process. It should further be appreciated that the virtual reality or augmented reality based device 704 may have a camera associated therewith used to image the real world and provide it to the user when operating in an augmented reality mode (Block 803).

One way to proceed with this simulation begins with acquiring a diagnostic representation of the bone (Block 804). This may be performed using an image capturing device associated with the electronic computing device 702, such as a two dimensional or three dimensional camera, or this may be performed using a standalone image capturing device and then receiving the image data from that device at the electronic computing device 702. Still further, this may be performed using a medical imaging device, such as a CT scan or MRI scan, and then receiving that image data at the electronic computing device 702, which may serve as apparatus 300.

Thereafter, the diagnostic representation of the bone is aligned with a suitable reference point (Block 805). Then, an insertion point of for a simulated surgical hardware installation is designated on the diagnostic representation of bone (Block 806). Next, an orientation of the simulated surgical hardware installation on the diagnostic representation of bone relative to reference point is determined (Block 807).

This orientation is determined in three dimensions, and can be referenced to suitable planes of the body as defined by typical medical terminology and known to those of skill in the art.

Figure 10:
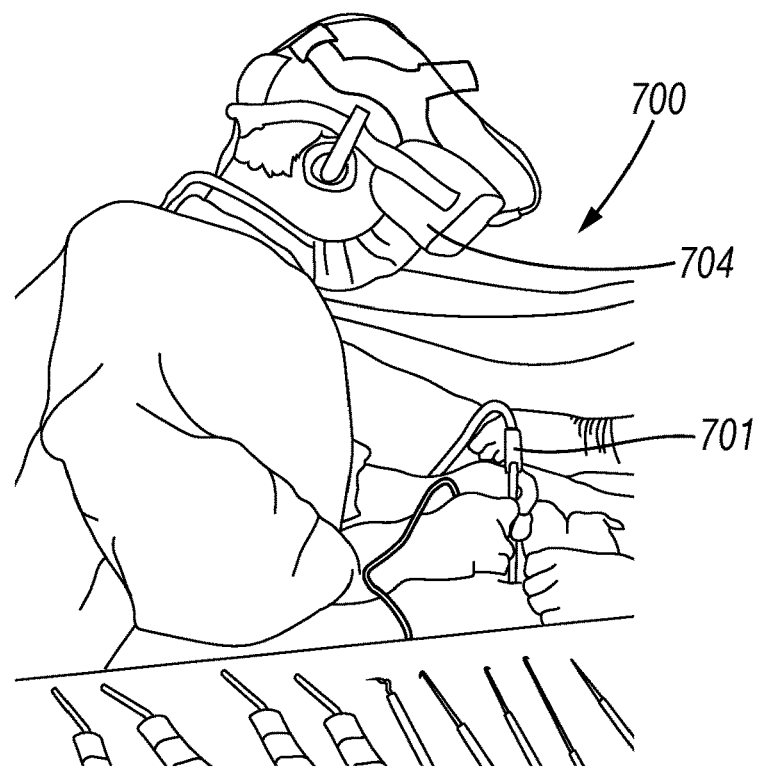
FIG. 10 illustrates the system of FIG. 8 in use to assist with inserting a medical device in a bone.
Figure 11:
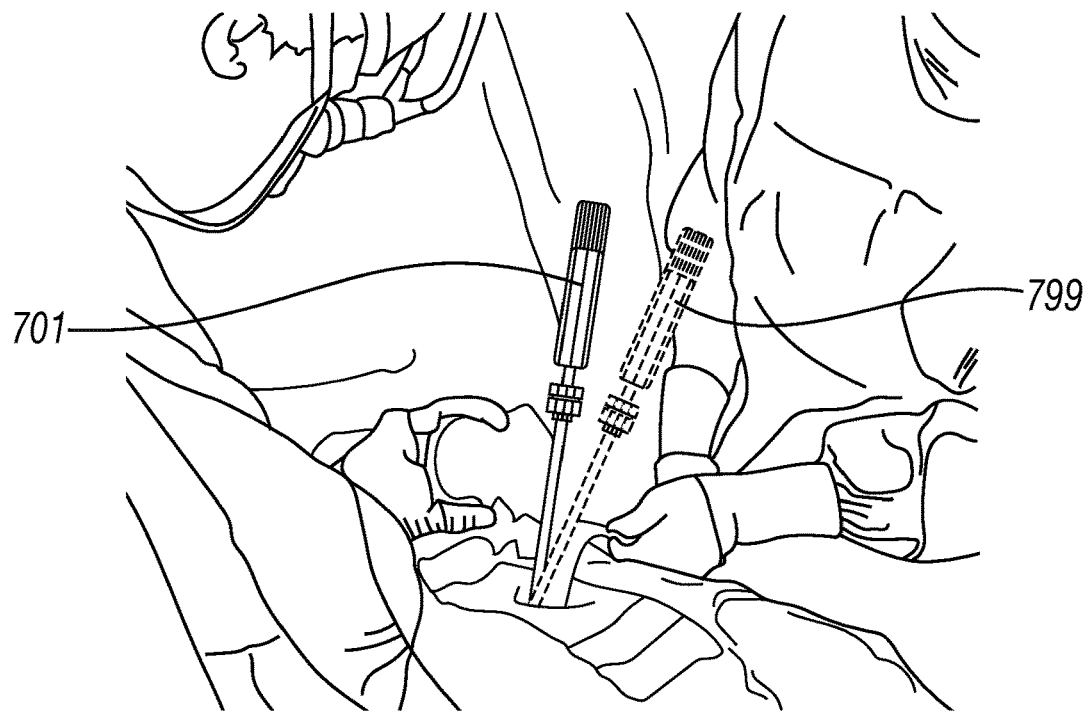
FIG. 11 illustrates an augmented reality display presented by the system of FIG. 8 showing an orientation angle for an instrument for inserting a medical device in a bone.

Then, the surgery itself may be performed. During surgery, virtual reality based or augmented reality based device 704 is worn by the operating physician or surgeon, as shown in FIG. 10. Here, the virtual reality or augmented reality based electronic device 704 is used to align an instrument or tool 701 for inserting a surgical hardware installation at a desired orientation through an insertion point of the bone by displaying visual indicia indicating the insertion point and the orientation of the simulated surgical hardware installation (Block 803). This visual indicia can be shown superimposed over the bone itself, such as shown in FIG. 11 by the virtual representation of the tool 799. It should be appreciated that the visual indicia need not be a virtual representation of the tool 799 as shown, and may instead be an arrow, a line, or any other suitable visual representation.

In some instances, cameras, position detectors, or other devices situated about the surgery site may be used to gather real time information about the actual position of the tool 701, so that feedback may be presented to the surgeon. For example, the visual indicia may change when the tool 701 is properly aligned, or may inform the surgeon that the tool 701 is not properly aligned. Likewise, additional visual indicia may be displayed when the tool 701 is properly aligned, or when the tool 701 is not properly aligned. Similarly, an audible response may be played by the virtual reality based or augmented reality based device 704 either when the tool 701 is properly aligned, or when the tool 701 is not properly aligned, or to guide the surgeon in moving the tool 701 into the proper position. In some cases, a position detector may be associated with or collocated with the tool 701, and the position detector such as an accelerometer may be used in determining whether the tool 701 is properly aligned, or when the tool 701 is not properly aligned.

In some instances, based on the above feedback, if the patient moved or the bone is moved, the visual indicia 799 is moved along with the bone by the virtual reality based or augmented reality based device 704 so that proper alignment is maintained during the surgery.

Figure 8:
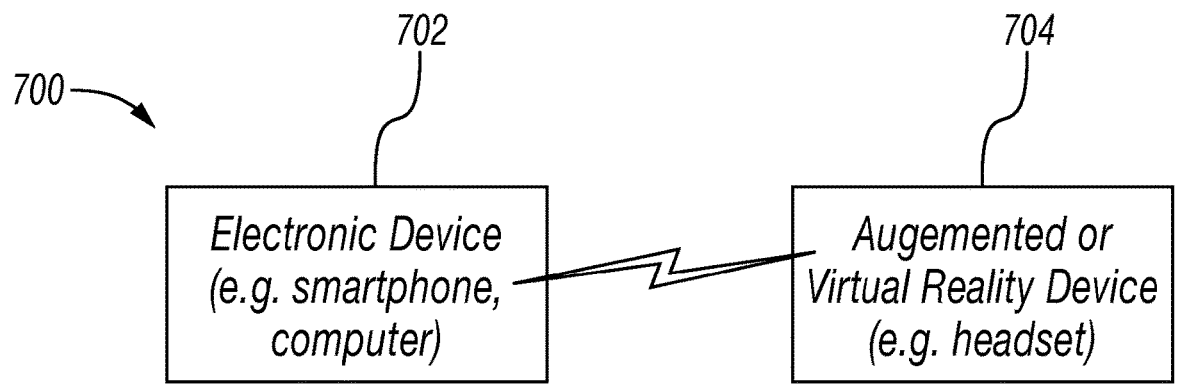
FIG. 8 presents a schematic diagram of a system used in accordance with an embodiment to define and verify an insertion angle for a pilot hole in a vertebra.
Figure 12:
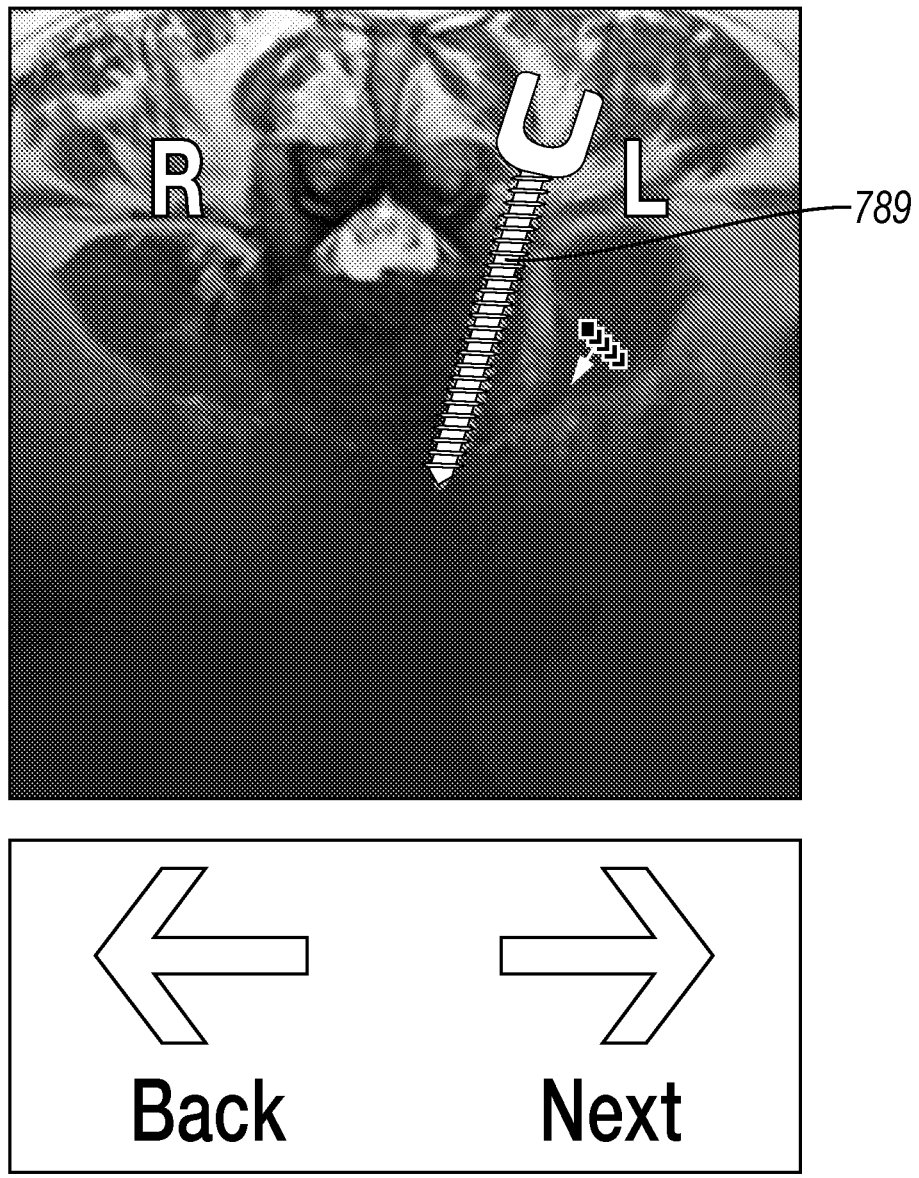
FIG. 12 illustrates a virtual representation presented by the system, such as the medical alignment device or electronic device of FIG. 8, showing an axial view of a vertebra with a proposed alignment position of a pedicle screw shown that includes an insertion point and alignment angle for insertion or installation of the medical device into the bone or vertebra in this plane.

FIG. 12 illustrates a virtual representation presented by the system, such as the medical alignment device or electronic device of FIG. 8, showing a diagnostic image of a vertebra in an axial view with a simulated pedicle screw 789 shown that can be manipulated and moved to set a desired insertion point or location, and a desired alignment angle. Once set, an insertion location and alignment angle are stored, such as by a medical alignment device 300, for this two-dimensional view of the vertebra or object in this plane.

Figure 13B:
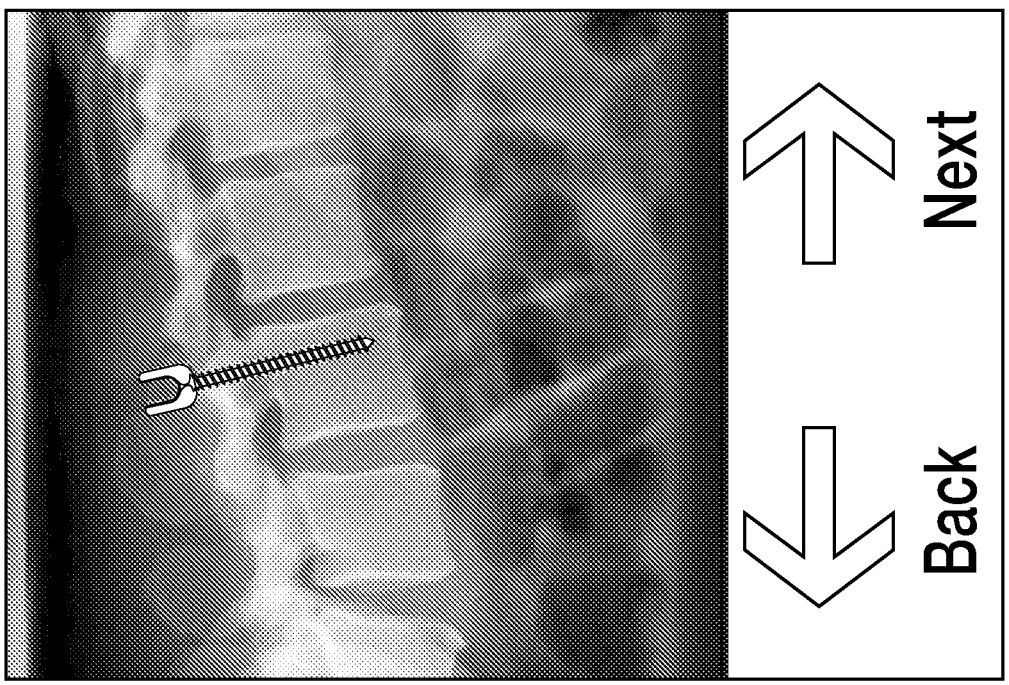
FIGS. 13A and 13B illustrate a virtual representation showing an orthogonal, lateral view of the vertebra and pedicle screw as set in the plane of FIG. 12, with the user able to establish the insertion location and alignment angle of the pedicle screw to be set in this plane so that the system, such as a medical alignment device, now has enough information as to the location of the pedicle screw in two orthogonal planes to determine a three-dimensional alignment angle for the installation of the pedicle screw in this vertebra.
Figure 13A:
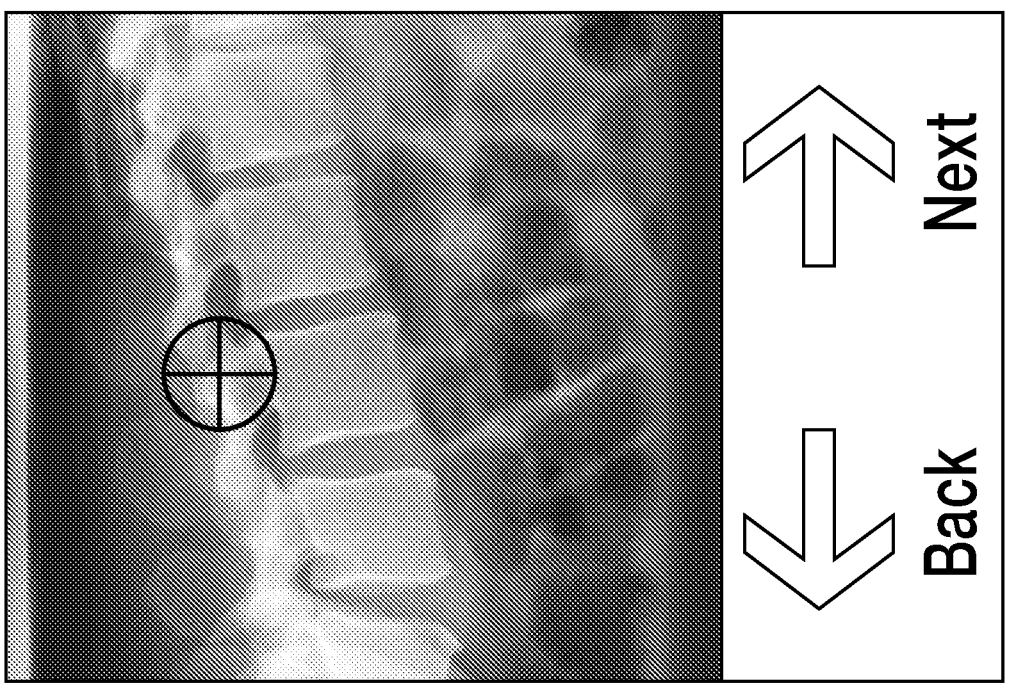

FIGS. 13A and 13B illustrate a virtual representation showing an orthogonal, lateral view of the vertebra and pedicle screw as shown and as set in the plane of FIG. 12, with the user able to establish or set the insertion location and alignment angle of the simulated pedicle screw in this plane so that the system, such as a medical alignment device, now has enough information as to the location of the pedicle screw in two orthogonal planes to determine a three-dimensional alignment angle for the installation of the pedicle screw (or drilling of a pilot hole for the pedicle screw) in this vertebra. FIG. 13A illustrates the cross-hair to set the desired insertion point, while being constrained with the positioning of the pedicle screw as defined in the view of FIG. 12, and, similarly, the angle of the pedicle screw may be set as desired as shown in FIG. 13B, while also being constrained with the positioning of the pedicle screw as set in the view of FIG. 12.

The medical alignment device 300 may calculate a desired three-dimensional alignment angle based on the inputs as just described in connection with FIGS. 12 and 13. The medical alignment device 300, knowing its own orientation, may notify a user, such as a surgeon, when a side, surface, or portion of the medical alignment device 300 is oriented according to the desired three-dimensional alignment angle. Thus, the apparatus 300, which may be referred to as a medical alignment device 300 in certain implementations, may be positioned relative to a tool (such as adjacent to or abutted with) to align the tool to the desired three-dimensional alignment angle. The tool may include, for example, a drill or gear shift probe to create a pilot hole for installing a pedicle screw. The tool, of course, could be any tool to be aligned at a desired three-dimensional angle.

Figure 14:
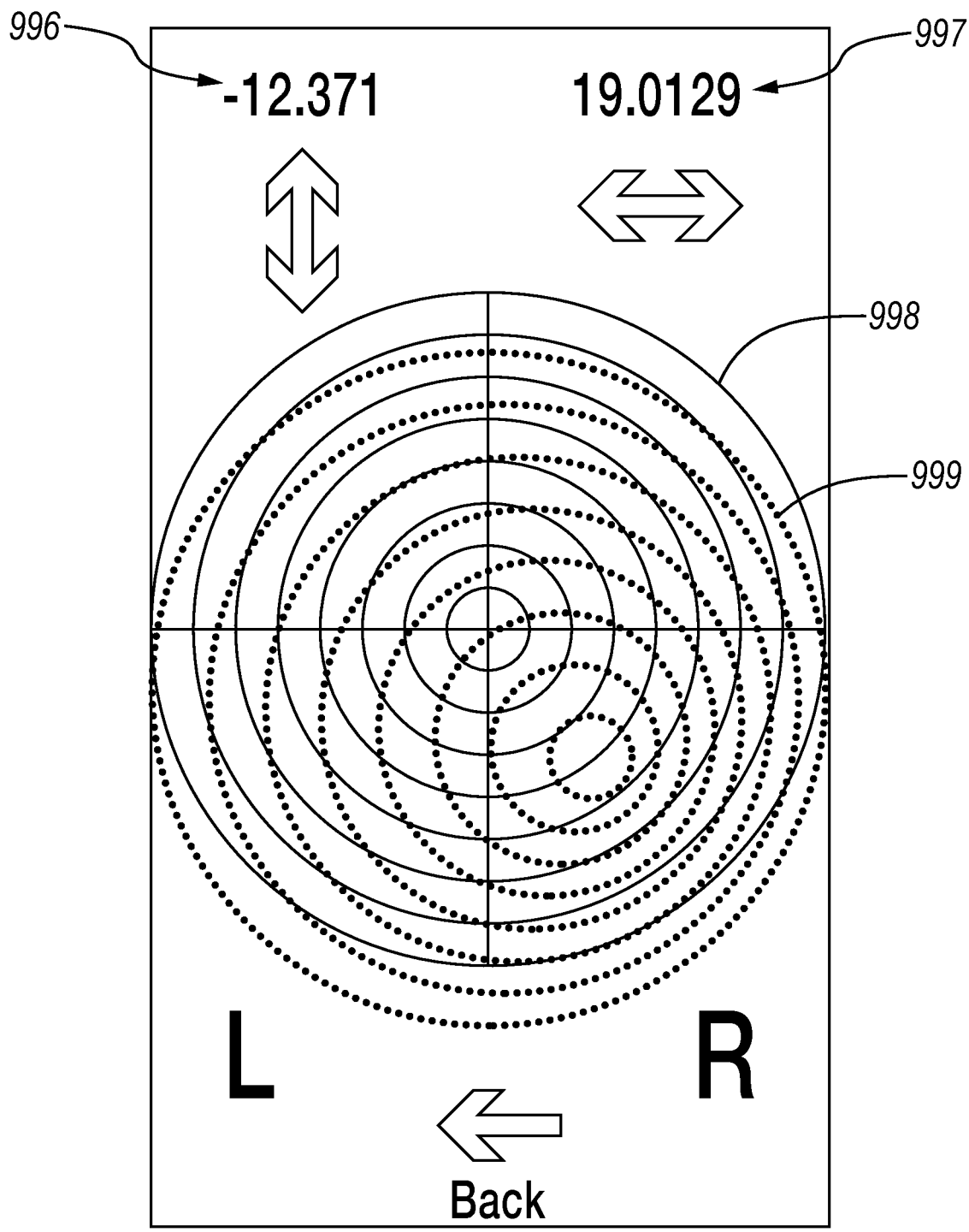
FIG. 14 illustrates an example application of the aligning method presented in FIG. 5A in which the medical device is not properly angled for insertion into the bone.
Figure 15:
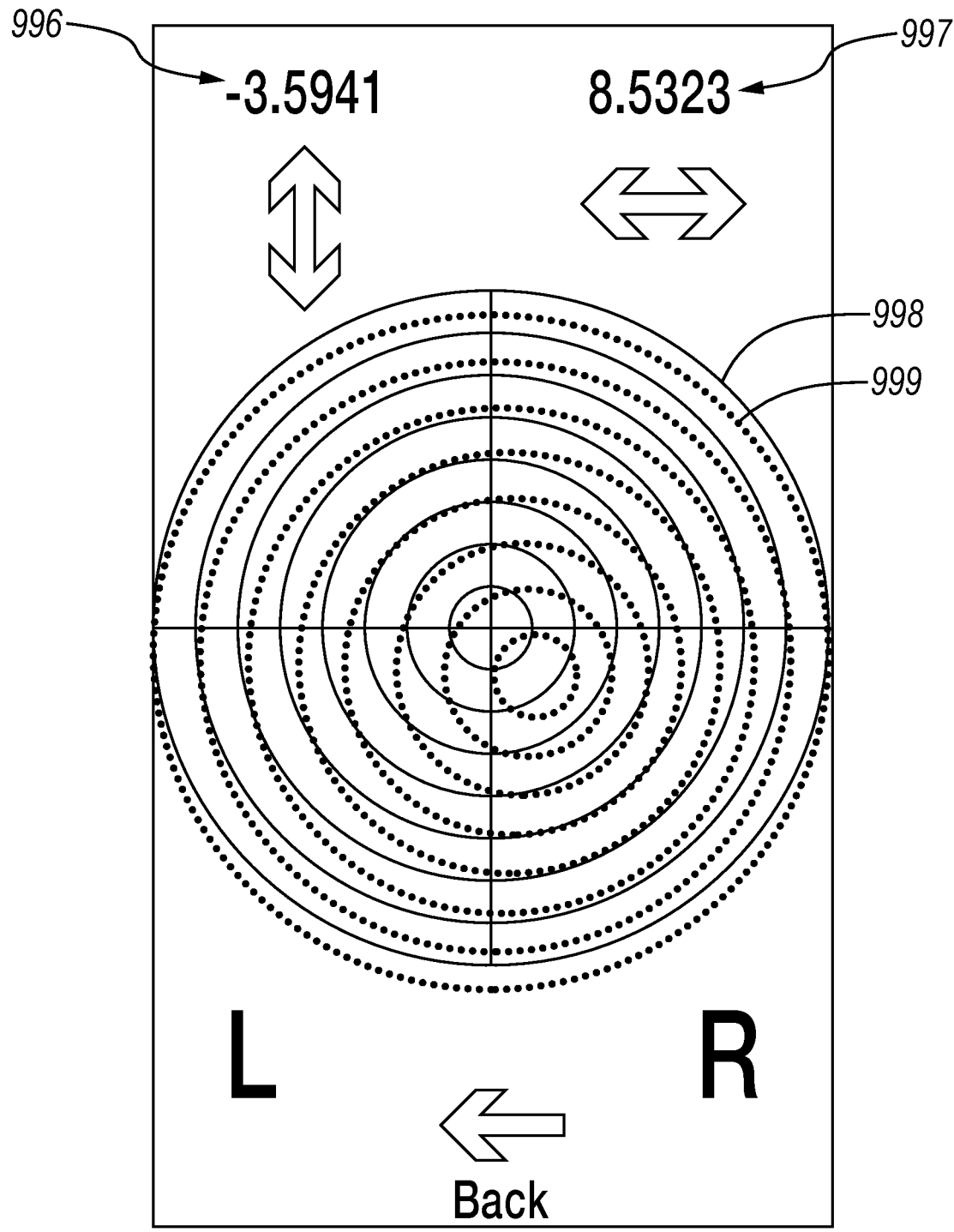
FIG. 15 illustrates an example application of the aligning method presented in FIG. 5A in which the medical device is not properly angled for insertion into the bone, yet is more properly aligned than it was in FIG. 14.
Figure 16:
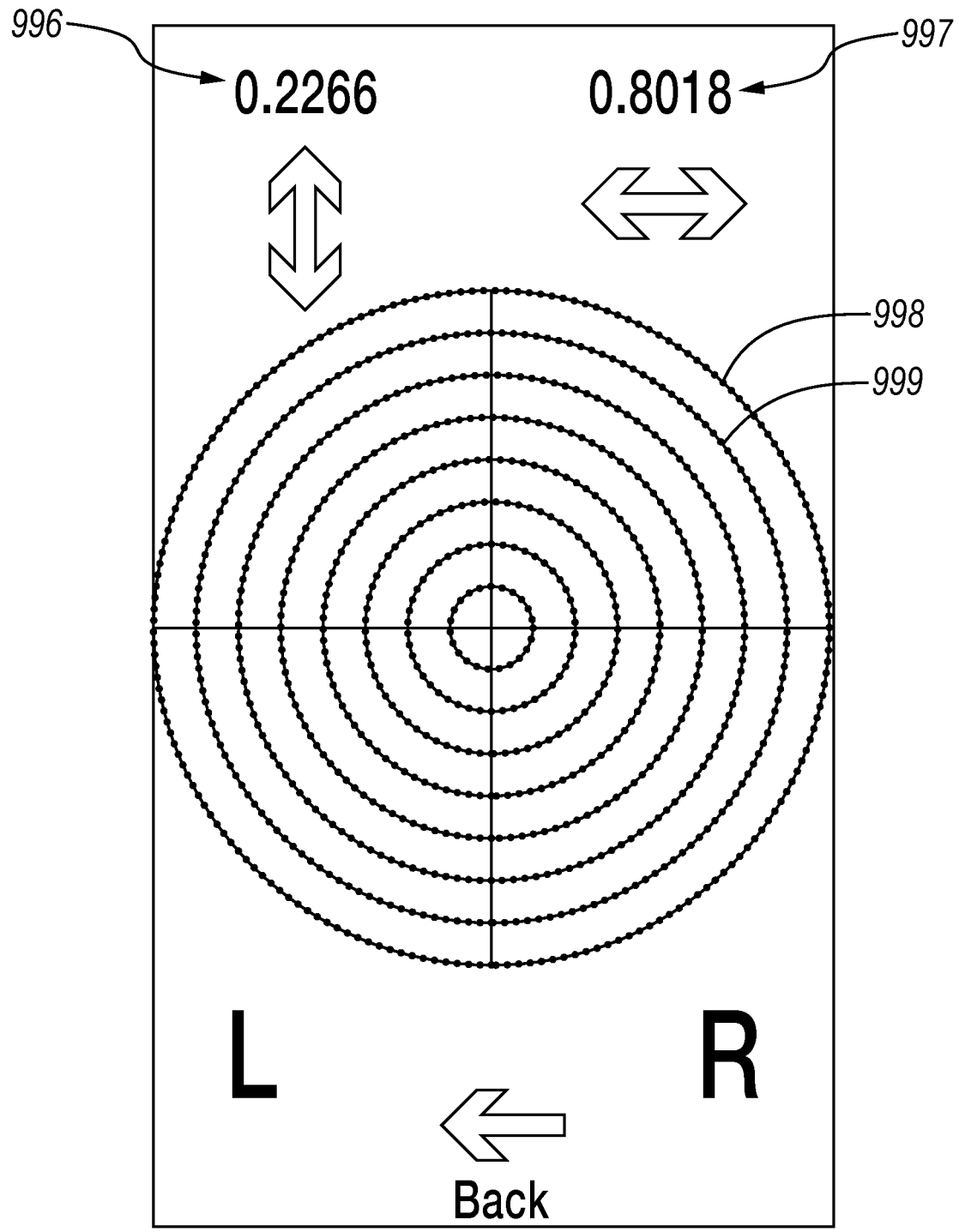
FIG. 16 illustrates an example application of the aligning method presented in FIG. 5A in which the medical device is properly angled for insertion into the bone.

FIGS. 14-16 illustrate a series of two-sets of concentric circles illustrating one embodiment of a graphical indicator or notification showing how the current position of the apparatus 300 is oriented relative to the desired alignment angle. As the orientation of the apparatus 300 is moved or aligned more closely to the desired three-dimensional alignment angle, as illustrated when looking at FIGS. 14-16 consecutively, the concentric circles are moved closer to one another providing a graphical indication or feedback to assist a user or surgeon to align the apparatus 300, and hence an attached or adjacent tool, to the desired alignment angle. Once the apparatus 300 is oriented within a desired threshold close to the three-dimensional alignment angle, an auditory, visual, and/or tactile notification may be provided to alert the user.

Numerical indicators 996 and 997 may also be provided as shown in FIGS. 14-16, along with double arrows adjacent the numerical indicators to denote alignment in each such plane. The apparatus 300 may display numerical differences (or errors) in each of the two planes of the desired alignment angles. The numerical indicators 996 and 997 show how close and in what direction the orientation of the apparatus 300 is positioned relative to the desired alignment angles in each of the two planes or two-dimensions as previously set and stored in the apparatus 300.

For example, FIG. 14 is a sample display of the apparatus 300 with two sets of concentric circles 998 and 999. In one implementation, the set of concentric circles 998 represents the desired three-dimensional alignment angle or orientation, such as the orientation of a pilot hole for a pedicle screw, while the set of concentric circles 999 represents the current three-dimensional orientation of the apparatus 300 showing the current orientation of the apparatus 300. As the apparatus 300 is oriented closer and closer to the desired three-dimensional alignment angle in FIGS. 15 and 16, the set of concentric circles 999 moves closer to the set of concentric circles 998 until the sets of circles are positioned over one another, or within a specified threshold, as illustrated in FIG. 16, to indicate that the apparatus 300 is aligned according to the desired three-dimensional alignment angle.

Similarly, the numerical indicators 996 and 997 in each of their respective planes are shown moving closer to zero, or within a specified threshold, as the apparatus 300 is moved closer and closer to the three-dimensional alignment angle when viewing FIGS. 14-16.

In one implementation, FIG. 15 is a sample display of the apparatus 300 in generating an indicator on the display 310 that indicates a degree of alignment between a tool aligned with a pedicle screw (or pilot hole or tool to install the pedicle screw) and the desired alignment angle, which may include an insertion sagittal angle, transverse angle, and/or coronal angle between an axis of the apparatus 300 and the sagittal plane, transverse plane, or coronal plane of the vertebra. As can be seen in FIG. 15, the indicator is in the form of a first set of concentric circles 998 and a second set of concentric circles 999. As the degree of alignment between the pedicle screw and the insertion sagittal angle, transverse angle, or coronal angle between an axis of the apparatus and the sagittal plane, transverse plane, or coronal plane of the vertebrae changes, the position of the first set of concentric circles 998 and position of the second set of concentric circles changes 999, or the position of one of the sets of the concentric circles 998 or 999 changes with respect to the other.

For example, as shown in FIG. 15, the set of concentric circles 999 is moved and positioned downward and to the right with respect to the set of concentric circles 998. This indicates that the proper alignment has not been found. By reorienting the apparatus 300, which it is noted would be directly or indirectly coupled to the pedicle screw or pilot hole location, in the appropriate direction, the set of concentric circles 999 moves closer to alignment with the set of concentric circles 998, as shown in FIG. 16. Once the proper alignment of the pedicle screw and the desired three-dimensional insertion angle between an axis of the apparatus and the vertebra has been reached, the sets of concentric circles 998 and 999 overlap one another, becoming one and the same, as shown in FIG. 16.

It can be noted that the color of the concentric circles 998 and 999 may be changed to further illustrate the degree of alignment between apparatus 300 and the desired alignment angle. For example, the misalignment indicated in FIG. 14 could be indicated by the set of concentric circles 999 being red, with the set of concentric circles 998 being blue; the better, but still not ideal, alignment indicated in FIG. 15 could be indicated by the set of concentric circles changing from red to yellow; and the ideal alignment indicated in FIG. 16 can be shown with both sets of concentric circles 998 and 999 being green.

It should be appreciated that although concentric circles have been shown, any concentric shapes can be used instead. In addition, concentric shapes need not be used, and any two individual shapes of the same size, or of a different size, may be used. Furthermore, it should be appreciated that in some instances one set of shapes may deform with respect to one another, in other instances both sets of shapes may remain at their original dimensions during operation.

In addition, in some instances, numerical indicators 996 and 997 may indicate the degree of alignment between the apparatus and a desired angle in a plane, a two-dimensional angle, such as the desired insertion sagittal angle, transverse angle, or coronal angle.

Figure 17:
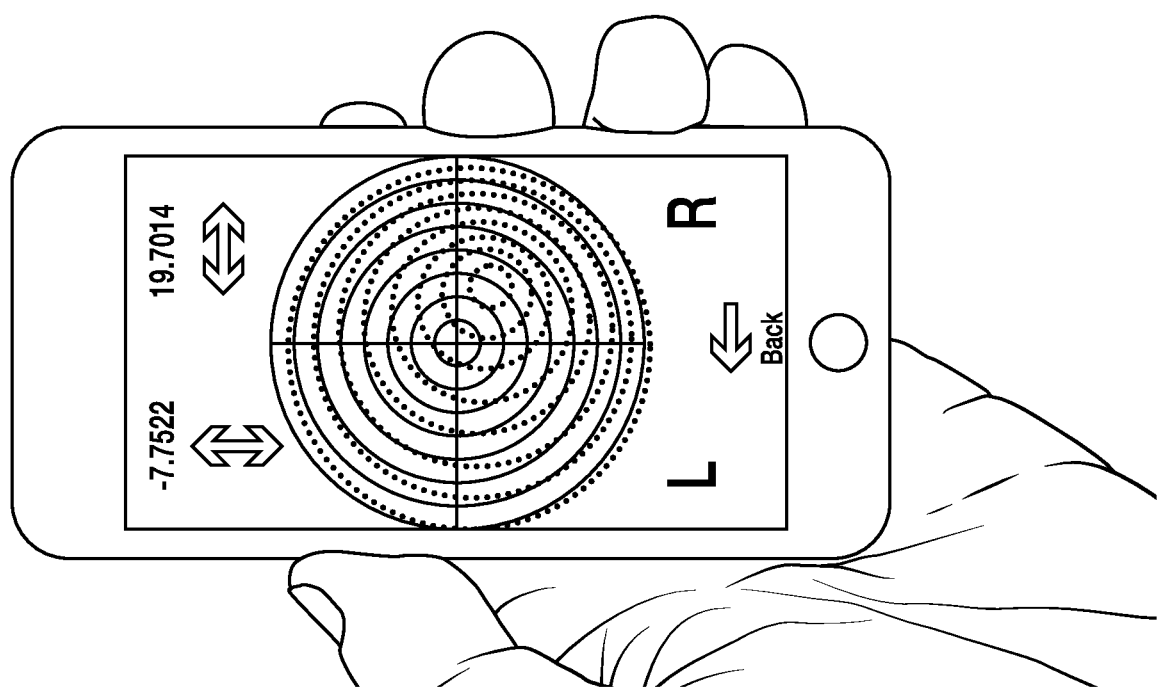
FIG. 17 illustrates the example applications shown in FIGS. 14-16 in operation on a smartphone.

FIG. 17 illustrates the example of implementing the apparatus 300 as a smartphone or smart device application, with the sets of concentric circles and numerical indicators displayed and showing relative alignment of the apparatus 300 with a desired alignment angle, such as was shown in FIGS. 14-16. The apparatus 300 includes orientation circuitry/apparatus, such as a gyroscope, to know its three-dimensional orientation.

Figure 18:
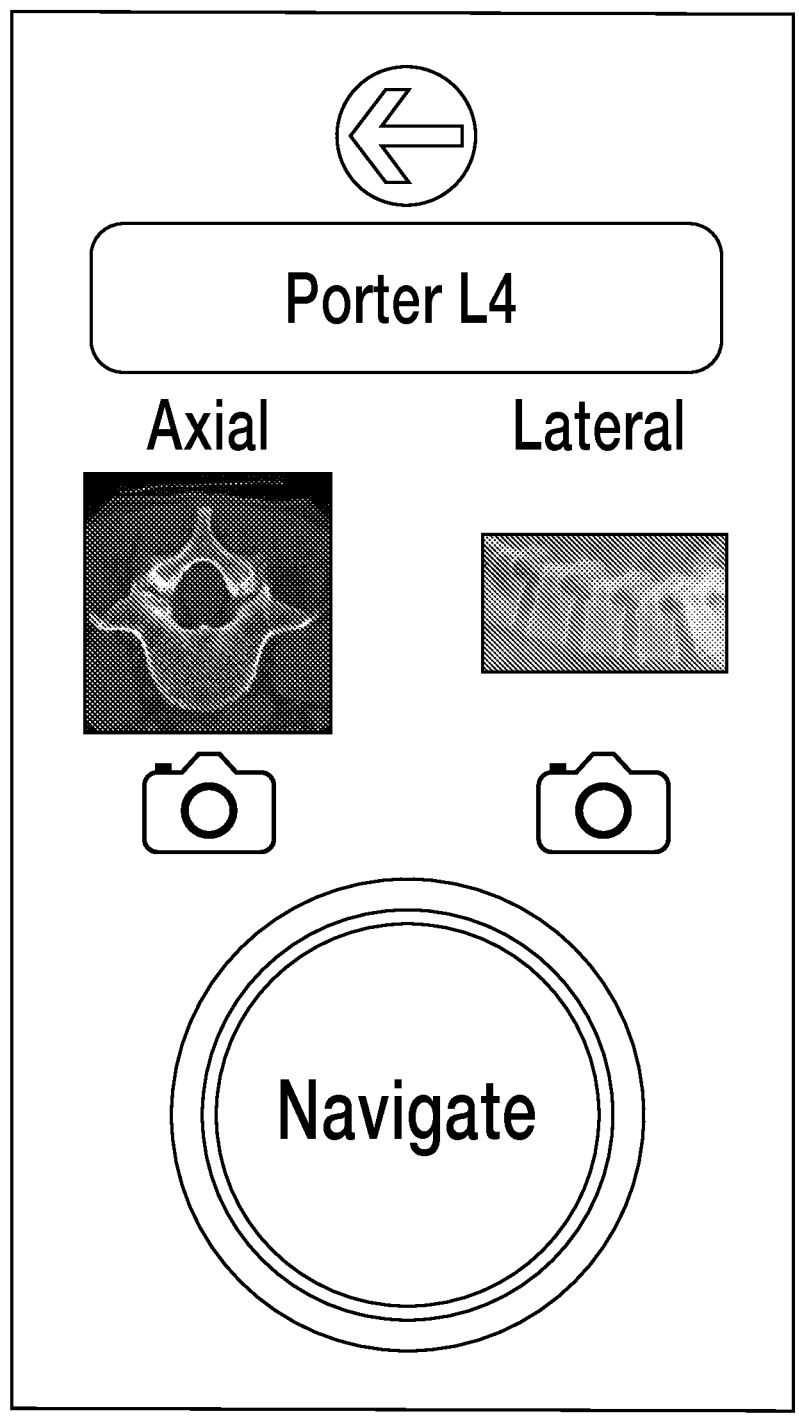
FIG. 18 illustrates a user interface of the device of FIG. 3A in operation when selecting different views of a bone.

Shown in FIG. 18 is a user interface of the apparatus 300 of FIG. 3A in operation when selecting different diagnostic image views of a vertebra that are orthogonal to one another in preparation for establishing desired alignment angles so that the three-dimensional alignment angle may be determined to install a pedicle screw. Also, a patient may be identified, as well as the specific vertebra is identified. The diagnostic images may be provided to the apparatus 300 by digital transmission, or by using a camera of the apparatus 300 to capture these two images of the vertebra that are orthogonal to one another.

Figure 19:
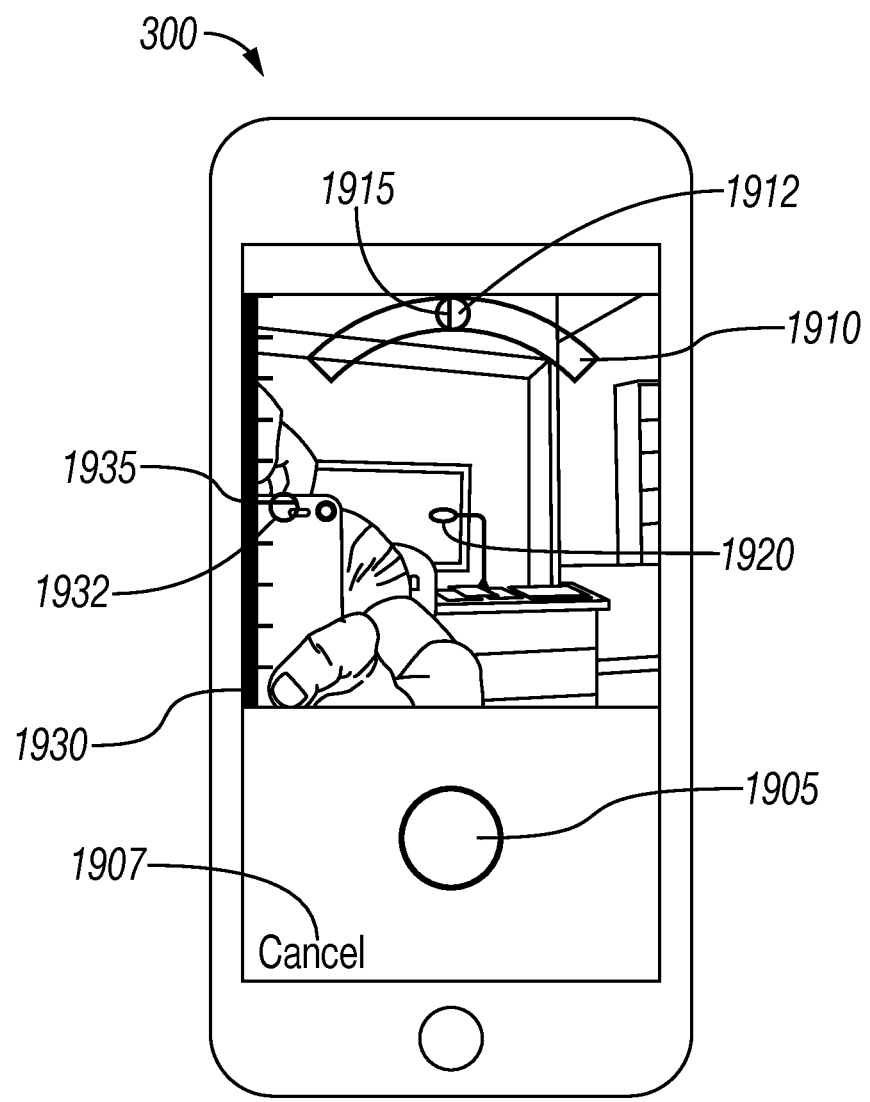
FIG. 19 illustrates a graphical user interface (GUI) of an orientation calibration system when the medical alignment device is properly oriented.

FIG. 19 illustrates a graphical user interface (GUI) of an orientation calibration system implemented using a smart device, such a smartphone, iPhone, iPod Touch, iPad, tablet computer, and the like. For example, the orientation calibration system may be implemented as part of the medical alignment device 300 (also referred to as apparatus 300 or orientation calibration system 300) to ensure that the medical alignment device is properly oriented or aligned when acquiring an image, such as a diagnostic image, appearing on an external display monitor. The diagnostic image may be acquired using a camera (not shown, and located on the other side) of the apparatus 300. The user interface may include a capture button 1905 (which may be thought of, or function as, a shutter button of a digital camera), a cancel button 1907, and an active viewfinder (the display capturing a live or current view using the camera of the device). For example, the diagnostic image to be captured may be displayed on a monitor as shown in the live view in FIG. 19 in the user interface. The display monitor shown in the live view is external to the apparatus 300 and may be referred to as an imaging source 1920. This may be a monitor to display any image, such as for example, a diagnostic medical image such as a CT or MRI scan. Inside the viewfinder or display of the apparatus 300, one or more graphical elements, such as dynamic graphical elements, may be provided to aid in displaying the present orientation of the apparatus 300, which may include a gyroscope or some other orientation sensor. In the illustrated example, dynamic graphical element includes a circle 1912 movable in a curved track 1910. The circle 1912 may change its color when the difference between the present orientation of the apparatus 300 and reference orientation is within a threshold value. The curved track 1910 may be indicated with a center position 1915, for which the user is intended to align the circle 1912. The tilt of the apparatus 300 to the left or right, in one implementation, should move the circle in each direction in the curved track 1910. This dynamic graphical element may be referred to as a left/right indicator, alignment, or orientation of the apparatus 300, and detects orientation, rotation, or alignment along, for example, a first axis, such as a "z" axis extending into and out of the page. This determines the position or orientation of the apparatus 300 along at least one axis.

The dynamic graphical element may further include a vertical indicator, such as a vertical gauge 1930 indicating a tilt of the medical alignment device 300 into or out of the page, in one implementation. The vertical gauge 1930 may include a center position 1935 and a circle 1932 movable along or adjacent the vertical gauge 1930. When the center (or some desired portion) of the circle 1932 reaches the center position 1935, the medical alignment device 300 becomes vertical and aligned with the gravitational direction (also referred to as orthogonal to the ground) or some other desired reference direction. This dynamic graphical element may be referred to as an up/down indicator, alignment, or orientation of the apparatus 300, and detects orientation, rotation, or alignment along, for example, a second axis, such as an "x" axis extending left to right on the page (or horizontal to the ground with the ground at the bottom of the page). This determines the position or orientation of the apparatus 300 along at least one axis.

Figure 20:
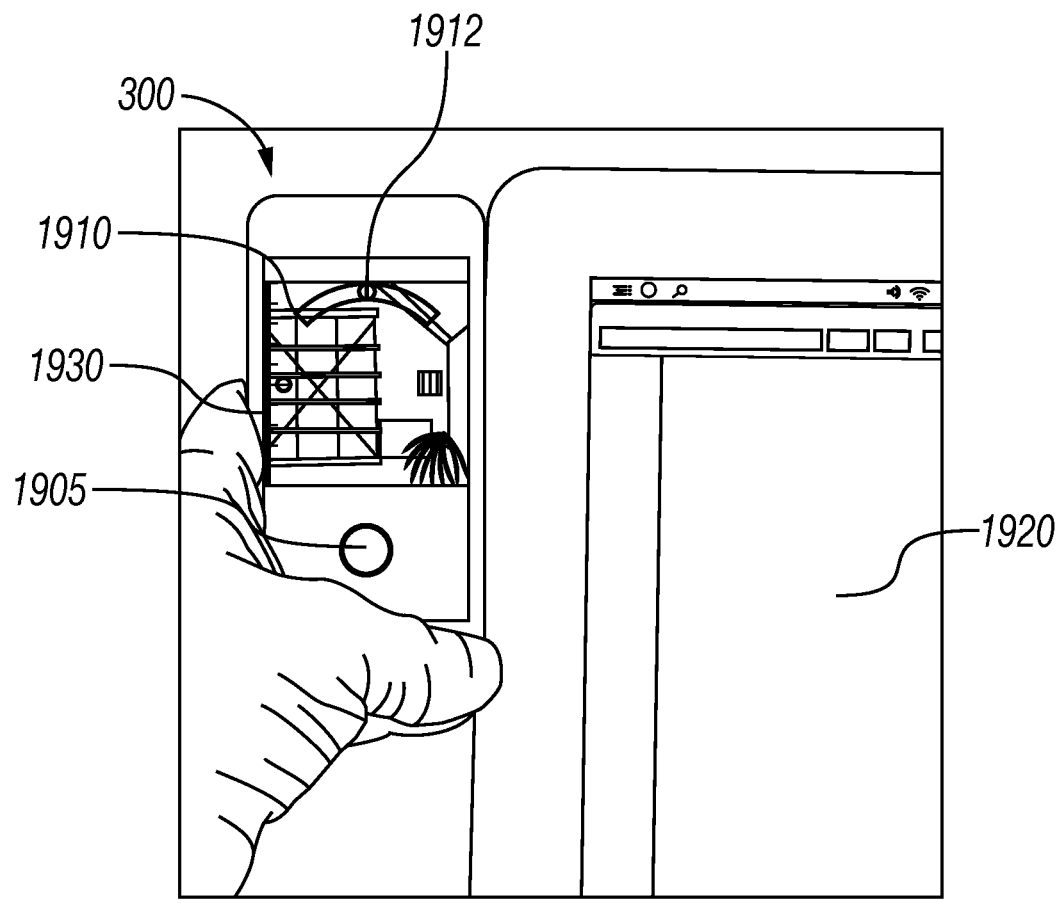
FIG. 20 illustrates an operation of using an orientation calibration system to calibrate an imaging source.

FIG. 20 illustrates an operation of using an orientation calibration system 300 to calibrate or align an imaging source 1920, which may be a computer monitor, external monitor, or any object where a target image is located. In certain applications, such as medical applications, having the imaging source 1920, such as a monitor displaying a diagnostic medical image that will be used in a medical alignment device, the need to ensure that the imaging source 1920 is properly oriented or aligned so that the image is not skewed when taken or captured by the medical alignment device. As shown, the imaging source 1920 is calibrated or adjusted to a desired orientation. This may be achieved by utilizing the orientation sensor of the apparatus 300 with a built in orientation sensor and the dynamic graphical elements described above. This apparatus 300 may be placed adjacent (or abutted against) certain sides, edges, or locations of the imaging source 1920 to ensure that the imaging source may be adjusted and aligned as desired. In one example, the apparatus 300 is first aligned to a known edge or side of the imaging source 1920 such that, in one example, they are coplanar and having at least one edge aligned, adjacent, and/or abutting one another as shown in FIG. 20.

The orientation sensor in the apparatus 300 may be active and shows the present orientation relative to a known reference orientation, such as a calibrated orientation or the ground. In some embodiments, the user may use the present orientation as the calibrated orientation or redefine the calibrated orientation, in certain implementations. The user may adjust the orientation of both the apparatus 300 and the imaging source 1920 to desired position or orientation. In one embodiment, the user desires that the display screen of the imaging source 1920 is perpendicular to the ground and all sides of the imaging source 1920 are orthogonal to one another and to the ground. This may be achieved, in one embodiment by (i) aligning the edge of the apparatus 300 adjacent a straight, left edge of the imaging source 1920, as shown, and adjusting the imaging source 1920 using the circle 1912 and the curved track 1910 until the left edge of the imaging source 1920 is vertical and orthogonal to the ground, and (ii) aligning the back of the apparatus 300 adjacent the flat face (or surface) of the display screen of the imaging source 1920, as shown, and adjusting the orientation of the imaging source 1920 using the circle 1932 and the vertical gauge 1930 until the face of the display screen of the imaging source 1920 is vertical and orthogonal to the ground. As such, two axes of rotation are aligned, and the imaging source 1920 may display a target image, such as a medical diagnostic image, that is positioned orthogonal to the ground. The apparatus 300 may then be used to capture or take a picture of that image displayed on the imaging source 1920 while the apparatus 300 itself, including the camera of the apparatus 300, is positioned orthogonally to the ground as well. This enhances the accurate capture of such target image, and reduces skew or errors, which are often not readily visible, that are introduced by capturing images at angles that are not properly aligned.

In some embodiments, a default orientation may be used, such as one of the sagittal plane, the transverse plane, the coronal plane, or planes orthogonal to the ground. The user may report the calibrated orientation by noting the relative positions between the circle 1912 and the curved track 1910, in the circle 1932 and the vertical gauge 1930. If the apparatus 300 captures the target image from the imaging source 1920 at the same default orientation, an accurate target image may be obtained.

Figure 21:
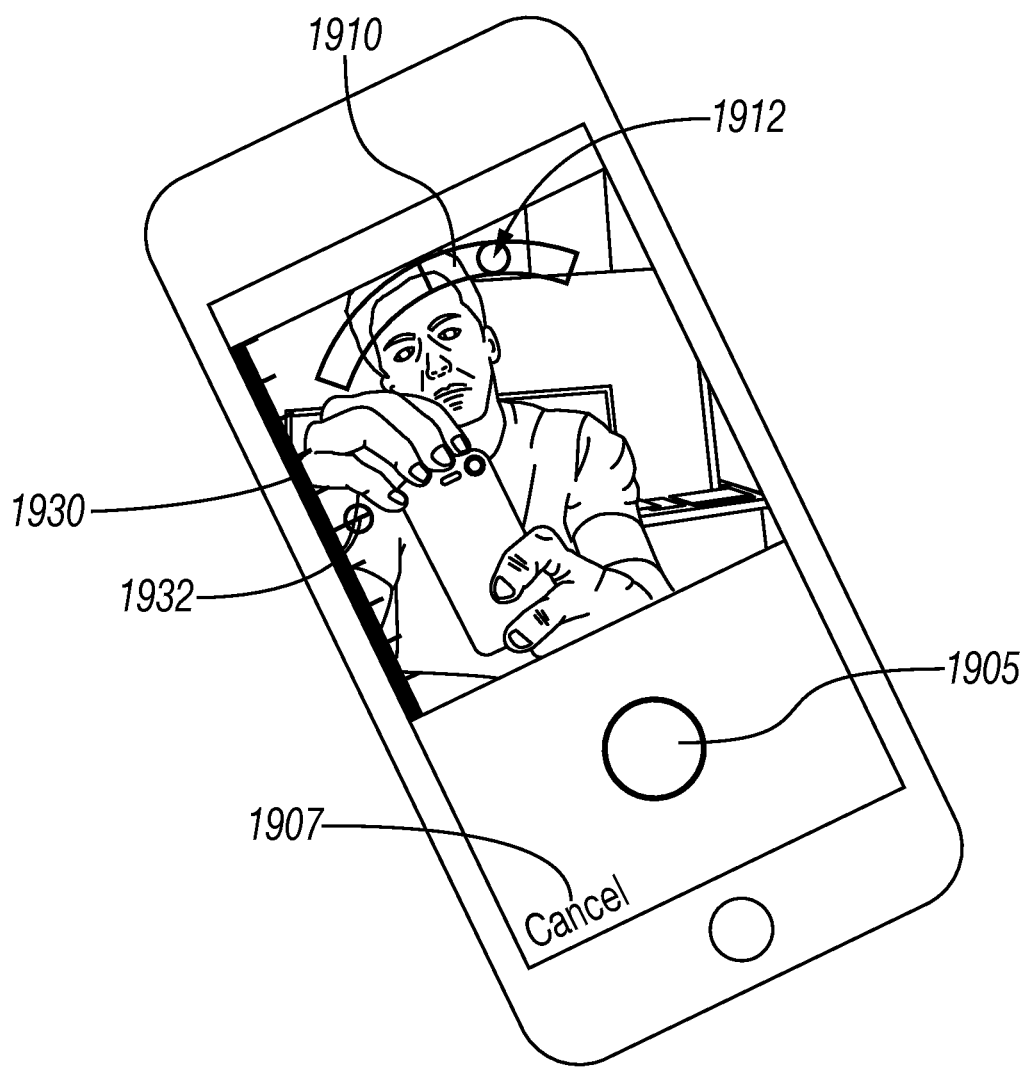
FIG. 21 illustrates a GUI of an orientation calibration system when the medical alignment device is out of the proper orientation.

FIG. 21 illustrates a GUI, such as that shown in FIG. 19, of an orientation calibration system when the medical alignment device 300 (which may also be referred to as the apparatus 300 or the orientation calibration system 300) is out of the proper or desired orientation. Because the apparatus 300 is shown tilted to the "left" on the page while positioned on a flat surface parallel to the ground, for example, the circle 1912 is far away from the center 1915 on the track 1910 indicating the "left" orientation of the apparatus 300, while the circle 1932 is positioned in the middle or adjacent the center position of the vertical gauge 1930 indicating that the back surface of the apparatus 300 is orthogonal to the ground. If the apparatus was tilted to the "right", the circle 1912 would be on the other side from the center 1915 on the track 1910 indicating the "right" orientation of the apparatus 300 in such a case.

Once the imaging source 1920 is properly oriented, a user may use the apparatus 300 to capture a target image displayed on the imaging source 1920. In doing so, it is important that the apparatus 300, which includes a camera, is properly aligned when capturing such target image. Thus, the same alignment tools of the apparatus 300 used to align and properly orient the imaging source 1920, including the dynamic graphical elements such as the circle 1912 and the curved track 1910 as well as the circle 1932 and the vertical gauge 1930, may be used to ensure that the apparatus 300 itself is properly oriented before the target image is captured by the apparatus 300. It should be understood that the present disclosure is not limited to the specific dynamic graphical elements illustrated herein, and that any number of other dynamic graphical elements may be used to ensure a desired orientation or alignment of the apparatus 300. For example, the curved track 1910 may be a straight track.

Figure 22:
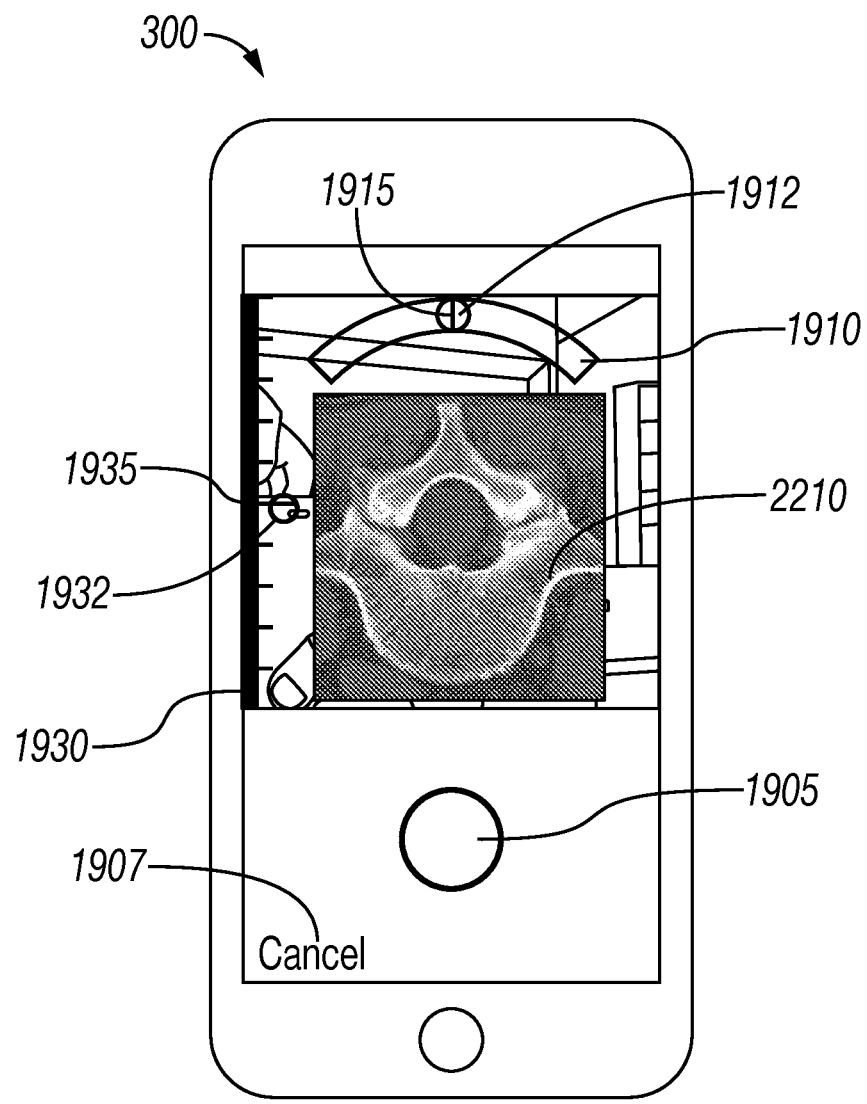
FIG. 22 illustrates an operation of using an orientation calibration system to capture a reference image from an imaging source.

FIG. 22 illustrates an operation of using the orientation calibration system 300 to capture a target image, which may also be referred to as a reference image 2210, from an imaging source, such as a display or monitor with a diagnostic image being displayed. For example, when the apparatus 300 is properly oriented, such as when the circle 1912 reaches a predetermined range or threshold near or adjacent the center 1915, and when the circle 1932 reaches a predetermined range or threshold of the center 1935, the reference image 2210 may be captured by the camera of the apparatus 300. In some embodiments, the processor of the medical alignment device 300 can automatically capture the reference image 2210 when alignment is achieved. In some other embodiments, in response to the alignment, a user can capture the reference image 2210 by pressing the capture button 1905. If a capture reference image 2210 is not satisfactory, a user may cancel to capture reference image 2210 by operation of the cancel button 1907.

Figure 23:
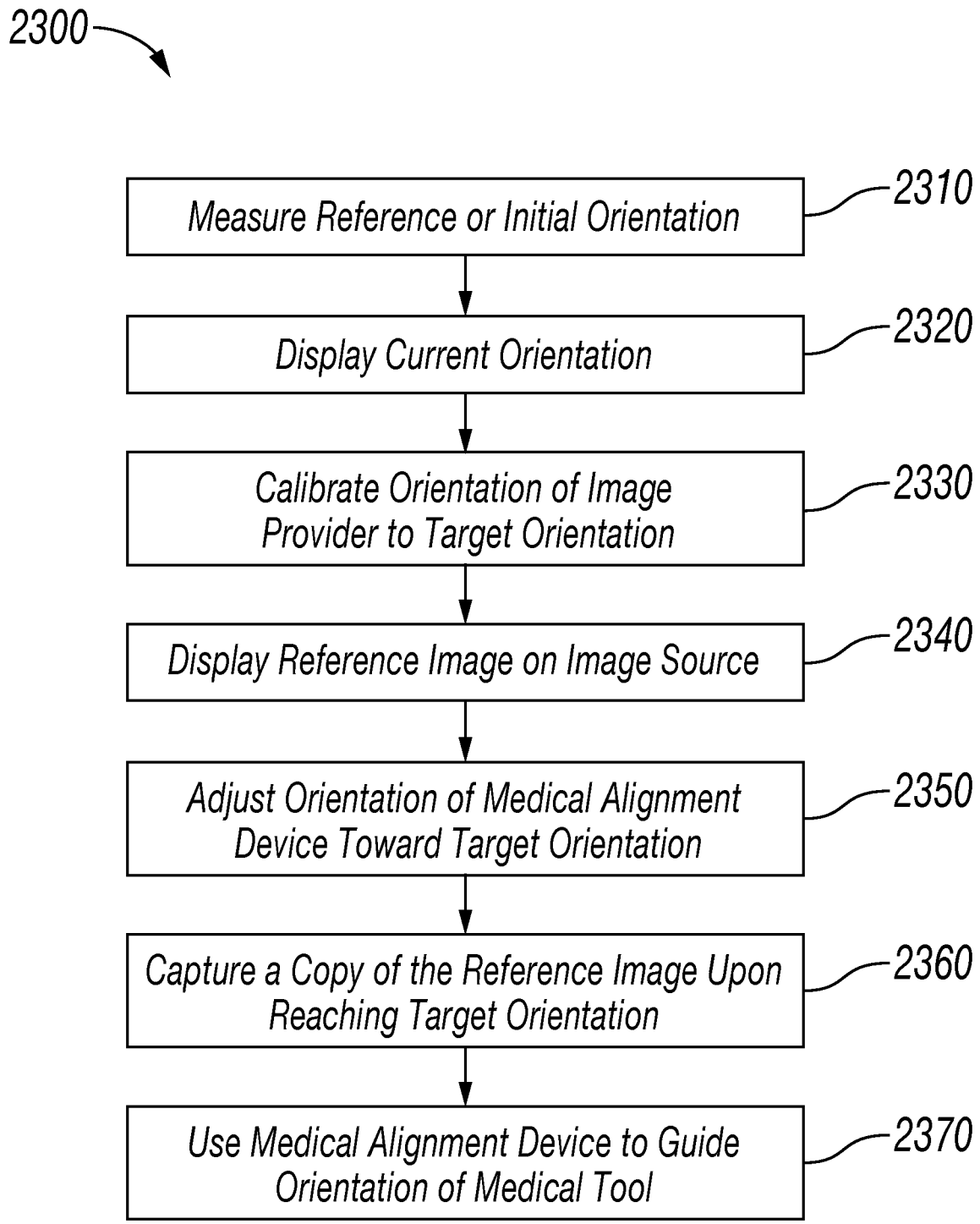
FIG. 23 is a flowchart showing an example of an orientation calibration process.

FIG. 23 is a flowchart 2300 showing an example of an orientation calibration process that may include one or more of a method for orienting a system for capture of a target image (or reference image), and a method for using an orientation calibration system to align a display monitor in an orthogonal position relative to the ground.

At 2310, the reference or initial orientation is measured. For example, the reference orientation may be an initial orientation recorded by the orientation sensor of the medical alignment device 300. Some embodiments, the reference orientation may be a specific orientation defined by the user relative to a known reference frame. Subsequent measurement of the orientation change by the orientation sensor may be made with reference to the measured reference orientation. In one embodiment, the reference orientation is already set and does not have to be set each time, and this may include a first axis orthogonal to the ground (a gravitational vector axis), with two additional axis each orthogonal to each other and each orthogonal to the first axis. This may be visualized as an x,y,z cartesian coordinate system in three-dimensional space.

At 2320, the current orientation of the apparatus 300 is displayed on a display screen of device, which may be an orientation calibration system or a medical alignment device, which we will use in describing the flowchart 2300. In some embodiments, the current orientation may be displayed when other visual devices, wirelessly or by cable, are in communication with the medical alignment device. The current orientation may be represented by a dynamic graphical representation, such as a circle moving along a track or gauge or numerically. The current orientation of the medical alignment device may be shown, in one implementation, as two or three axis of rotation, and this information is provided by an orientation sensor using a gyroscope in the medical alignment device 300.

At 2330, the user calibrates the orientation of the imaging source, which may be a computer monitor, to a target orientation. For example, the target orientation may be the sagittal plane, the transverse plane, and the coronal plane, or orthogonal to the ground along a side edge, and parallel to the ground along a top or bottom edge.

At 2340, a reference image or target image is displayed by the imaging source, such as a display monitor. For example, an imaging source may be connected to a CT scanner that provides images of a patient. In some other embodiments, the imaging source may be connected to a database storing images of the patient.

At 2350, orientation of the medical alignment device 300 is adjusted to the target orientation so that when the target image is captured by the camera of the apparatus 300, the image will not be distorted or skewed. For example, a user may hold the medical alignment device 300 and view the dynamic graphical representations of its current orientation on its display, such as by tracking the circles along a curved track or the vertical gauge as shown in FIGS. 19-22, until a camera of the medical alignment device 300 is properly aligned in front of the target image to properly capture such image being displayed by the imaging source.

At 2360 when a target orientation is reached, a copy of the reference or target image may be captured by the medical alignment device. For example, the processor of the medical alignment device 300 may capture the reference image automatically when the target orientation is reached. In other instances, a user may provide a command to capture the reference image in response to reaching the target orientation. The command may be by touch, may be by voice, and may include other sources of inputs.

At 2370, the now calibrated medical alignment device 300, in certain implementations, may be ready to guide orientation of the medical tool, for example, as discussed in FIG. 7.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed is:
1. An orientation calibration system for image capture, the orientation calibration system comprising:
    a camera operable to capture a target image;
    a display screen configured to display the target image captured using the camera;

an orientation sensor configured to determine at least two axes of rotation of the orientation calibration system; and one or more processors configured to:
ascertain a present orientation of the orientation calibration system using the orientation sensor;
display at least a portion of the present orientation of the orientation calibration system and a desired orientation of the orientation calibration system on the display screen;
receive a request to capture the target image; and
capture the target image using the camera in response to receiving the request to capture the target image, and when a difference between the present orientation of the orientation calibration system and the desired orientation of the orientation calibration system is within a threshold;
wherein the target image that is being captured is displayed on an external monitor having four sides with each adjacent side being orthogonal to one another, and the orientation calibration system includes a first side and a back side, and is configured to assist in aligning the external monitor in an orthogonal position relative to the ground before the target image is captured by the orientation calibration system, the one or more processors of the orientation calibration system further configured to:
display a left/right graphical indicator when the first side of the orientation calibration system is positioned along a side edge of the external monitor to display an indication from the orientation sensor of the present left/right orientation of the orientation calibration system and a desired left/right orientation of the external monitor, wherein the left/right graphical indicator changes as the left/right orientation of the external monitor is adjusted while the first side of the orientation calibration system is positioned along the side edge of the external monitor and the present left/right orientation of the orientation calibration system changes; and
display an up/down graphical indicator when the back side of the orientation calibration system is positioned along a front surface of the external monitor to display an indication from the orientation sensor of the present up/down orientation of the orientation calibration system and a desired up/down orientation of the external monitor, wherein the up/down graphical indicator changes as the up/down orientation of the external monitor is adjusted while the back side of the orientation calibration system is positioned along the front surface of the external monitor and the present up/down orientation of the orientation calibration system changes.

2. The orientation calibration system of claim 1, wherein the one or more processors are further configured to generate a notification when the difference between the present orientation of the orientation calibration system and the desired orientation of the orientation calibration system is within a threshold.

3. The orientation calibration system of claim 2, wherein the notification is generated by the orientation calibration system and may include at least one from the group that includes a visual notification on the display, an auditory notification using a speaker of the orientation calibration system, and a tactile notification to generate a vibratory movement.

4. The orientation calibration system of claim 1, wherein the one or more processors are further configured to generate a graphical element to display the at least a portion of the present orientation of the orientation calibration system and the desired orientation on the display screen, and wherein the graphical element includes a circle or object movable in a curved track on the display screen, and wherein the circle or object changes color when the difference between the present orientation of the orientation calibration system and the desired orientation of the orientation calibration system is within the threshold.

5. The orientation calibration system of claim 1, wherein the orientation calibration system is implemented as part of a medical alignment device.

6. The orientation calibration system of claim 1, wherein the one or more processors are configured to capture the target image upon receiving both the request to capture the target image, and after the difference between the present orientation of the orientation calibration system and the desired orientation of the orientation calibration system is within the threshold.

7. The orientation calibration system of claim 6, wherein the request to capture the target image is received after the difference between the present orientation of the orientation calibration system and the desired orientation of the orientation calibration system is within the threshold.

8. The orientation calibration system of claim 1, wherein the one or more processors are configured to automatically capture the target image upon receiving the request to capture the target image, and the difference between the present orientation of the orientation calibration system and the desired orientation of the orientation calibration system is within the threshold.

9. A method for using an orientation calibration system to align a display monitor in an orthogonal position relative to the ground, the display monitor having four sides with each adjacent side being orthogonal to one another and configured to display a target image, the method comprising:
positioning a first side of the orientation calibration system adjacent a first side of the display monitor;
determining an alignment of the first side of the display monitor using the orientation calibration system;
adjusting the alignment of the first side of the display monitor to ensure it is in the orthogonal position relative to the ground within an acceptable threshold as determined by the orientation calibration system;
positioning a back side of the orientation calibration system adjacent a front surface of the display monitor;
determining an alignment of the front surface of the display monitor using the orientation calibration system;
wherein the orientation calibration system displays an up/down graphical indicator when the back side of the orientation calibration system is positioned along the front surface of the display monitor to display an indication from an orientation sensor of a present up/down orientation of the orientation calibration system and a desired up/down orientation of the display monitor, wherein the up/down graphical indicator changes as a present up/down orientation of the display monitor is adjusted while the back side of the orientation calibration system is positioned along the front surface of the display monitor and the present up/down orientation of the orientation calibration system changes; and
adjusting the alignment of the front surface of the display monitor to ensure it is in the orthogonal position relative to the ground within an acceptable threshold as determined by the orientation calibration system.

10. The method for using the orientation calibration system to align the display monitor in the orthogonal position relative to the ground of claim 9, wherein the orientation calibration system displays a left/right graphical indicator when the first side of the orientation calibration system is positioned along the first side of the display monitor to display an indication of a present left/right orientation of the orientation calibration system and a desired left/right orientation of the display monitor, wherein the left/right graphical indicator changes as the left/right orientation of the display monitor is adjusted while the first side of the orientation calibration system is positioned along the first side of the display monitor and the present left/right orientation of the orientation calibration system changes.

\* \* \* \* \*